United States Patent
Suleiman et al.

(10) Patent No.: US 12,296,041 B2
(45) Date of Patent: May 13, 2025

(54) HAIR CARE COMPOSITIONS

(71) Applicant: L'OREAL, Paris (FR)

(72) Inventors: Azizah Khader Suleiman, Paterson, NJ (US); Prashansa Mayank Desai, Hoboken, NJ (US)

(73) Assignee: L'OREAL, Paris (FR)

( * ) Notice: Subject to any disclaimer, the term of this patent is extended or adjusted under 35 U.S.C. 154(b) by 140 days.

(21) Appl. No.: 17/244,368

(22) Filed: Apr. 29, 2021

(65) Prior Publication Data

US 2022/0354768 A1    Nov. 10, 2022

(51) Int. Cl.

| | | |
|---|---|---|
| A61K 8/891 | (2006.01) | |
| A45D 19/00 | (2006.01) | |
| A61K 8/34 | (2006.01) | |
| A61K 8/37 | (2006.01) | |
| A61K 8/60 | (2006.01) | |
| A61K 8/73 | (2006.01) | |
| A61K 8/81 | (2006.01) | |
| A61K 8/92 | (2006.01) | |
| A61Q 5/12 | (2006.01) | |

(52) U.S. Cl.
CPC ............ *A61K 8/891* (2013.01); *A45D 19/005* (2021.01); *A61K 8/342* (2013.01); *A61K 8/37* (2013.01); *A61K 8/375* (2013.01); *A61K 8/604* (2013.01); *A61K 8/731* (2013.01); *A61K 8/8188* (2013.01); *A61K 8/922* (2013.01); *A61K 8/927* (2013.01); *A61Q 5/12* (2013.01); *A61K 2800/48* (2013.01); *A61K 2800/5426* (2013.01)

(58) Field of Classification Search
CPC ...................................... A61K 8/891
See application file for complete search history.

(56) References Cited

U.S. PATENT DOCUMENTS

| | | | |
|---|---|---|---|
| 2011/0129431 A1 | 6/2011 | McDermott et al. | |
| 2013/0315846 A1 | 11/2013 | Collier et al. | |
| 2015/0139925 A1 | 5/2015 | Kamikawa et al. | |
| 2016/0235643 A1 | 8/2016 | Mathonneau et al. | |
| 2018/0116937 A1 | 5/2018 | Park et al. | |
| 2018/0235854 A1* | 8/2018 | Carle ........................ | A61K 8/60 |
| 2019/0201315 A1 | 7/2019 | Gevgilili et al. | |
| 2019/0343742 A1 | 11/2019 | Pattanaik et al. | |
| 2020/0000701 A1 | 1/2020 | Uribe et al. | |

FOREIGN PATENT DOCUMENTS

| | | | | |
|---|---|---|---|---|
| DE | 102007030099 A1 * | 1/2009 | ............... | A61K 8/06 |
| WO | WO-2009112492 A2 * | 9/2009 | ............... | A61K 8/06 |

OTHER PUBLICATIONS

Translation of DE 102007030099 A1 (Year: 2009).*
Mehraj et al. (Castor Oil and Cocoa Butter to Improve the Moisture Barrier and Tensile Properties of Pectin Films, Journal of Polymers and the Environment, 2022). (Year: 2022).*
https://www.jouvaychocolate.com/melting-cocoa-butter (Year: 2023).*
https://www.knowde.com/stores/seppic-inc/products/montanov-I (Year: 2019).*
https://www.anveya.com/blogs/ingredients-directory/octyldodecanol#:~:text=BENEFITS%20OF%20OCTYLDODECANOL&text=Acts%20as%20an%20emulsifier%3A%20It,to%20foam%20upon%20being%20shaken. (Year: 2021).*
https://cosmetics.specialchem.com/inci-ingredients/isopropyl-myristate (Year: 2014).*
Mintel report; Database "Shave-Control Scalp Lotion." 2014, pp. 1-5.
Preliminary Search Report and Written Opinion issued on Apr. 4, 2022 for corresponding French Application No. FR 2107841.

* cited by examiner

*Primary Examiner* — Andrew S Rosenthal
*Assistant Examiner* — Danielle Kim
(74) *Attorney, Agent, or Firm* — POLSINELLI PC

(57) ABSTRACT

Hair care compositions and methods for providing conditioning benefits to hair is disclosed. The hair care compositions may include one or more nonionic surfactants comprising one or more alkylpolyglucosides; one or more fatty alcohols; one or more fatty esters comprising caprylic/capric triglyceride; about 0.5 to about 30 wt. % of a fatty compound other than fatty alcohol and fatty ester; one or more silicones comprising polysilicone-11; one or more thickening agents; and water, wherein the hair care composition is an emulsion, and all weight percentages are based on the total weight of the hair care composition.

18 Claims, No Drawings

HAIR CARE COMPOSITIONS

FIELD OF THE DISCLOSURE

The present disclosure relates to hair care compositions and methods for providing conditioning benefits to hair.

BACKGROUND OF THE DISCLOSURE

Consumers desire new and improved compositions for treating, caring for, and/or conditioning keratinous substances, such as hair. Generally, hair is exposed to intrinsic and extrinsic influences such as environmental factors, mechanical factors, chemical factors, heat, and aging that damage the hair. For example, environmental factors, such as sun light and heat as well as mechanical or chemical treatments, such as brushing, combing, dyeing, bleaching, permanent-waving and/or relaxing, blow-drying, flat ironing, or even repeated washing can damage and weaken hair fibers. Over time, hair may become dry, coarse, brittle or dull, especially in fragile areas, and more particularly at the ends, resulting in split ends.

To overcome these drawbacks, it is common practice to resort to haircare products using compositions intended to condition the hair, giving it satisfactory cosmetic properties, especially in terms of smoothness, sheen, softness, suppleness, lightness, a natural feel and good disentangling properties. For example, hair care compositions, such as hair conditioner and/or treatment compositions, may be used before or after the hair has been washed with shampoo and/or subjected to a chemical treatment in order to improve or return to the hair its natural luster, shine, and softness, or to improve the feel, appearance, and manageability of hair.

It is understood that different forms of haircare compositions can provide different benefits. However, there is still a need for products that provide superior conditioning properties, while not weighing down the hair, leaving the hair greasy, and/or providing undesirable cosmetic properties.

SUMMARY OF THE DISCLOSURE

Aspects of the disclosure relates to hair care compositions that provide significant conditioning benefits to the hair. For example, certain embodiments of the compositions provide deep conditioning to hair while simultaneously repairing the damaged sites on the hair fiber. Additionally, the hair care compositions may be formulated as emulsions with large amounts of oils. The inventors discovered that unique combinations of ingredients in certain ratios surprisingly promotes emulsions that stably contain large amounts of oil. For instance, the inventors unexpectedly discovered that hair care compositions having the combination of alkylpolyglucosides comprising $C_{12-20}$ alkyl glucoside, fatty alcohols comprising $C_{14-22}$ alcohols, and an acrylic thickening agent comprising hydroxyethyl acrylate/sodium acryloyldimethyl taurate copolymer in certain weight ratios produced emulsions with significantly enhanced stability. It was further discovered that the hair care compositions achieved unexpected benefits when certain ingredients, such as caprylic/capric triglyceride and polysilicone-11, were combined with the remainder of the hair care compositions.

The hair care composition according to an aspect of the disclosure typically comprises:
(a) one or more nonionic surfactants comprising one or more alkylpolyglucosides;
(b) one or more fatty alcohols;
(c) one or more fatty esters comprising caprylic/capric triglyceride;
(d) about 0.5 to about 30 wt. % of a fatty compound other than a fatty alcohol and fatty ester;
(e) one or more silicones comprising polysilicone-11;
(f) one or more thickening agents; and
(g) water,
  wherein the hair care composition is an emulsion, and all weight percentages are based on the total weight of the hair care composition.

In some embodiments, the hair care compositions comprise:
(a) about 2 to about 15 wt. % of the one or more nonionic surfactants comprising one or alkylpolyglucosides chosen from $C_{12-20}$ alkyl glucoside;
(b) about 0.5 to about 5 wt. % of the one or more fatty alcohols, wherein the one or more fatty alcohols include $C_{14-22}$ alcohols;
(c) about 1 to about 15 wt. % of the one or more fatty esters comprising caprylic/capric triglyceride;
(d) about 0.5 to about 30 wt. % of a fatty compound other than fatty alcohol and fatty ester;
(e) about 0.5 to about 10 wt. % of the one or more silicones comprising polysilicone-11;
(f) about 0.1 to about 10 wt. % of the one or more thickening agent wherein the one or more thickening agent includes hydroxyethyl acrylate/sodium acryloyldimethyl taurate copolymer; and
(g) about 40 wt. % or more of water.

The fatty alcohols of the hair care composition may comprise octyldodecanol in addition to $C_{14-22}$ alcohols. The hair care compositions may have a weight ratio of the total amount of $C_{12-20}$ alkyl glucoside and $C_{14-22}$ alcohols to the total amount hydroxyethyl acrylate/sodium acryloyldimethyl taurate copolymer is about 0.1:1 to about 1:0.1. In some instances, the weight ratio of the total amount of $C_{14-22}$ alcohols and $C_{12-20}$ alkyl glucoside to the total amount hydroxyethyl acrylate/sodium acryloyldimethyl taurate copolymer is about 0.5:1 to about 1:0.5.

Additionally or alternatively, the hair care compositions may be formulated to contain a total amount of oil is about 1 to 20 wt. %, based on the weight of the hair care composition. The fatty compound other than fatty alcohol and fatty ester may include about 0.1 to about 10 wt. % of a wax. For example, the hair care composition may include a wax is chosen from illipe butter, beeswax, butyrospermum parkii (shea) butter, euphorbia cerifera wax, carnauba, lanolin, lanolin derivatives, candelilla, cocoa butter, sugar cane wax, montan wax, whale wax, bayberry wax, acacia decurrents flower wax, vegetable waxes, and a mixture thereof.

Non-limiting examples of suitable fatty esters include cetyl ester, purcellin oil, isopropyl myristate, isopropyl palmitate, glyceryl stearate, caprylic/capric triglyceride, sorbitan isostearate, $C_{12}$-$C_{15}$ alkyl benzoate, 2-ethylphenyl benzoate, isopropyl lanolate, hexyl laurate, diisopropyl adipate, isononyl isononanoate, oleyl erucate, 2-ethylhexyl palmitate, isostearyl isostearate, diisopropyl sebacate, octanoates, decanoates or ricinoleates of alcohols or polyalcohols, hydroxylated esters, dicaprylyl carbonate, pentaerythritol esters, or a mixture thereof. In at least one case, the one or more fatty esters comprise isopropyl myristate and caprylic/capric triglyceride.

The hair care composition may include one or more silicones comprising dimethicone, dimethiconol, decamethylcyclopentasiloxane, cyclomethicone, or a mixture thereof in addition to the polysilicone-11.

Additionally or alternatively, the hair care composition may further include about 3 to about 20 wt. % of a polyol. The polyol may be chosen from ethylene glycol, propylene glycol, butylene glycol, hexylene glycol, pentylene glycol, diethylene glycol, dipropylene glycol, 1,3 propanediol, glycerin, polyethylene glycols, and a mixture thereof.

In some cases, the hair care composition further includes about 0.01 to about 10 wt. % of a cationic polymer. Examples of cationic polymers include, but are not limited to, polyquaternium-4, polyquaternium-6, polyquaternium-7, polyquaternium-10, polyquaternium-11, polyquaternium-16, polyquaternium-22, polyquaternium-28, polyquaternium-32, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, guar hydroxypropyltrimonium chloride, or a mixture thereof.

In accordance with another aspect of the disclosure, a method is provided for improve hair. The method typically includes:
(I) applying a hair care composition to hair, the hair care composition comprising:
   (a) one or more nonionic surfactants comprising one or more alkylpolyglucosides;
   (b) one or more fatty alcohols;
   (c) one or more fatty esters comprising caprylic/capric triglyceride;
   (d) about 0.5 to about 30 wt. % of a fatty compound other than a fatty alcohol and fatty ester;
   (e) one or more silicones comprising polysilicone-11;
   (f) one or more thickening agents; and
   (g) water,
      wherein all weight percentages are based on the total weight of the hair care composition,
(II) optionally, rinsing the hair care compositions from the hair.

The hair care composition of the method may have a weight ratio of the total amount of $C_{12-20}$ alkyl glucoside and $C_{14-22}$ alcohols to the total amount hydroxyethyl acrylate/sodium acryloyldimethyl taurate copolymer is about 0.1:1 to about 1:0.1. In some instances, the hair care composition may include a silicone chosen from dimethicone, dimethiconol, decamethylcyclopentasiloxane, cyclomethicone, and a mixture thereof in addition to the polysilicone-11.

DETAILED DESCRIPTION OF THE DISCLOSURE

The present disclosure generally relates to hair care compositions and methods that provide significant conditioning benefits to the hair. Desirably, certain embodiments of the compositions provide deep conditioning to hair while simultaneously repairing the damaged sites on the hair fiber.

Additionally, the inventors discovered that unique combinations of ingredients in certain ratios promotes emulsions that stably contain large amounts of oil. Thus, certain embodiments of the hair care compositions unexpectedly contain large amounts of oils in a stable oil-in-water emulsion. For example, the inventors unexpectedly discovered that hair care compositions having the combination of $C_{12-20}$ alkyl glucoside, $C_{14-22}$ alcohols, and hydroxyethyl acrylate/sodium acryloyldimethyl taurate copolymer in certain weight ratios produced emulsions with enhanced stability. It was further discovered that the hair care compositions achieved unexpected benefits when certain ingredients, such as caprylic/capric triglyceride and polysilicone-11, were combined with the remainder of the hair care compositions.

The hair care compositions according to an aspect of the disclosure typically comprise:
(a) one or more nonionic surfactants comprising one or more alkylpolyglucosides;
(b) one or more fatty alcohols;
(c) one or more fatty esters comprising caprylic/capric triglyceride;
(d) about 0.5 to about 30 wt. % of a fatty compound other than a fatty alcohol and fatty ester;
(e) one or more silicones comprising polysilicone-11;
(f) one or more thickening agents; and
(g) water,
   wherein the hair care composition is an emulsion, and all weight percentages are based on the total weight of the hair care composition.

As used herein, an oil refers to compounds having a melting temperature of less than 35° C. and having a hydrophobic portion. For example, the hair care compositions may include oils chosen from fatty compounds, such as fatty alcohols (e.g., octyldodecanol), fatty esters (e.g., triglycerides), etc., as well as silicones, such as silicone polymers (e.g., dimethicone). In at least one instance, the oils present in the hair care composition are selected from the group consisting of fatty compounds, silicones, and a mixture thereof.

The total amount of oil (such as, oils chosen from fatty compounds and silicones) may be about 1 to about 20 wt. %, based on the total weight of the hair care composition. In some cases, the total amount of oil may be about 1 to about 20 wt. %, about 2 to about 20 wt. %, about 3 to about 20 wt. %, about 4 to about 20 wt. %, about 5 to about 20 wt. %, about 6 to about 20 wt. %, about 8 to about 20 wt. %, about 10 to about 20 wt. %, about 12.5 to about 20 wt. %, about 15 to about 20 wt. %; about 1 to about 18 wt. %, about 2 to about 18 wt. %, about 3 to about 18 wt. %, about 4 to about 18 wt. %, about 5 to about 18 wt. %, about 6 to about 18 wt. %, about 8 to about 18 wt. %, about 10 to about 18 wt. %, about 12.5 to about 18 wt. %, about 15 to about 18 wt. %; about 1 to about 16 wt. %, about 2 to about 16 wt. %, about 3 to about 16 wt. %, about 4 to about 16 wt. %, about 5 to about 16 wt. %, about 6 to about 16 wt. %, about 8 to about 16 wt. %, about 10 to about 16 wt. %, about 12.5 to about 16 wt. %, about 15 to about 16 wt. %, including any ranges and subranges therebetween, based on the total weight of the hair care composition.

Additionally or alternatively, the hair care compositions form an emulsion. For instance, the hair care compositions may be in the form of an oil-in-water emulsion.

Suitable components, such as those listed below, may be included or excluded from the formulations for the hair care compositions depending on the specific combination of other components, the form of the hair care compositions, and/or the use of the formulation.

Nonionic Surfactant(s)

The hair care compositions include one or more nonionic surfactant(s) comprising alkylpolyglucosides. In an embodiment, the hair care compositions include one or more nonionic surfactant(s) comprising $C_{12-20}$ alkyl glucoside which is commercially available as a blend with $C_{14-22}$ alcohols under the tradename of MONTANOV L from the company Seppic.

Typically, the hair care compositions include a total amount of nonionic surfactant(s) of about 1 to about 15 wt. %, based on the total weight of the hair care composition. For example, the hair care composition may include nonionic surfactants in an amount of about 1 to about 15 wt. %, about 1 to about 13 wt. %, about 1 to about 11 wt. %, about 1 to about 9 wt. %, about 1 to about 7 wt. %, about 1 to about 5 wt. %, about 1 to about 4 wt. %; about 2 to about 15 wt. %, about 2 to about 13 wt. %, about 2 to about 11 wt. %, about 2 to about 9 wt. %, about 2 to about 7 wt. %, about 2 to about 5 wt. %; about 3 to about 15 wt. %, about 3 to about 13 wt. %, about 3 to about 11 wt. %, about 3 to about 9 wt. %, about 3 to about 7 wt. %; about 4 to about 15 wt. %, about 4 to about 13 wt. %, about 4 to about 11 wt. %, about 4 to about 9 wt. %, about 4 to about 7 wt. %; about 5 to about 15 wt. %, about 5 to about 13 wt. %, about 5 to about 11 wt. %, about 5 to about 9 wt. %, about 5 to about 7 wt. %, about 6 to about 7 wt. %, include ranges and subranges therebetween, based on the total weight of the hair care composition.

The amount of $C_{12-20}$ alkyl glucoside present in the hair care composition may be about 0.05 to about 10 wt. %, based on the total weight of the hair care composition. In some instances, the amount of $C_{12-20}$ alkyl glucoside in the hair care composition may be about 0.05 to about 8 wt. %, about 0.05 to about 6 wt. %, about 0.05 to about 4 wt. %, about 0.05 to about 3 wt. %, about 0.05 to about 2 wt. %, about 0.05 to about 1 wt. %; about 0.1 to about 10 wt. %, about 0.1 to about 8 wt. %, about 0.1 to about 6 wt. %, about 0.1 to about 4 wt. %, about 0.1 to about 3 wt. %, about 0.1 to about 2 wt. %, about 0.1 to about 1 wt. %, include ranges and subranges therebetween, based on the total weight of the hair care composition.

In addition to $C_{12-20}$ alkyl glucoside, the hair care compositions may include other nonionic surfactants. In at least one embodiment, the other nonionic surfactants include PEG-40 hydrogenated castor oil and, optionally, polysorbate 60 in addition to alkylpolyglucosides.

The one or more nonionic surfactants in the hair care composition may include alkanolamides; alkyl polyglucosides; polyoxyalkylenated nonionic surfactants; polyglycerolated nonionic surfactants; ethoxylated fatty esters; and/or ethoxylated oils from plant origin. Non-limiting examples of nonionic surfactants other than alkylpolyglucosides include: alkanolamides; alkyl polyglucosides; polyoxyalkylenated nonionic surfactants; polyglycerolated nonionic surfactants; ethoxylated fatty esters; alcohols, alpha-diols, alkylphenols and esters of fatty acids, being ethoxylated, propoxylated or glycerolated; copolymers of ethylene oxide and/or of propylene oxide; condensates of ethylene oxide and/or of propylene oxide with fatty alcohols; polyethoxylated fatty amides; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives, amine oxides such as ($C_{10}$-$C_{14}$)alkylamine oxides or N—($C_{10}$-$C_{14}$) acylaminopropylmorpholine oxides; and mixtures thereof. In some cases, the plurality of nonionic surfactants can be useful.

Further discussion of nonionic surfactants other than alkylpolyglucosides that may be suitable in the hair care compositions is provided below:

(i) Alkanolamides

Non-limiting examples alkanolamides include fatty acid alkanolamides. The fatty acid alkanolamides may be fatty acid monoalkanolamides, fatty acid dialkanolamides, or fatty acid isoalkanolamides, and may have a $C_{2-8}$ hydroxyalkyl group (the $C_{2-8}$ chain can be substituted with one or more than one —OH group). Non-limiting examples include fatty acid diethanolamides (DEA) or fatty acid monoethanolamides (MEA), fatty acid monoisopropanolamides (MIPA), fatty acid diisopropanolamides (DIPA), and fatty acid glucamides (acyl glucamides).

Suitable fatty acid alkanolamides include those formed by reacting an alkanolamine and a C6-C36 fatty acid. Examples include, but are not limited to: oleic acid diethanolamide, myristic acid monoethanolamide, soya fatty acids diethanolamide, stearic acid ethanolamide, oleic acid monoisopropanolamide, linoleic acid diethanolamide, stearic acid monoethanolamide (Stearamide MEA), behenic acid monoethanolamide, isostearic acid monoisopropanolamide (isostearamide MIPA), erucic acid diethanolamide, ricinoleic acid monoethanolamide, coconut fatty acid monoisopropanolamide (cocoamide MIPA), coconut acid monoethanolamide (Cocamide MEA), palm kernel fatty acid diethanolamide, coconut fatty acid diethanolamide, lauric diethanolamide, polyoxyethylene coconut fatty acid monoethanolamide, coconut fatty acid monoethanolamide, lauric monoethanolamide, lauric acid monoisopropanolamide (lauramide MIPA), myristic acid monoisopropanolamide (Myristamide MIPA), coconut fatty acid diisopropanolamide (cocamide DIPA), and mixtures thereof.

In some instances, the fatty acid alkanolamides preferably include cocamide MIPA, cocamide DEA, cocamide MEA, cocamide DIPA, and mixtures thereof. In particular, the fatty acid alkanolamide may be cocamide MIPA, which is commercially available under the tradename EMPILAN from Innospec Active Chemicals.

Fatty acid alkanolamides include those of the following structure:

wherein,
- $R_4$ is an alkyl chain of 4 to 20 carbon atoms ($R_4$ may be, for example, selected from lauric acid, coconut acid, palmitic acid, myristic acid, behenic acid, babassu fatty acid, isostearic acid, stearic acid, corn fatty acid, soy fatty acid, shea butter fatty acids, caprylic acid, capric acid, and mixtures thereof);
- $R_6$ is selected from —$CH_2OH$, —$CH_2CH_2OH$, —$CH_2CH_2CH_2OH$, —$CH_2(CHOH)_4CH_2OH$, -benzyl, and mixtures thereof; and
- $R_6$ is selected from —H, —$CH_3$, —$CH_2OH$, —$CH_2CH_3$, —$CH_2CH_2OH$, —$CH_2CH_2CH_2OH$, —$CH_2(CHOH)_4CH_2OH$, -benzyl, and mixtures thereof.

In some instances, the one or more of the fatty acid alkanolamides include one or more acyl glucamides, for example, acyl glucamides having a carbon chain length of 8 to 20. Non-limiting examples include lauroyl/myristoyl methyl glucamide, capryloyl/capryl methyl glucamide, lauroyl methyl glucamide, myristoyl methyl glucamide, capryloyl methyl glucamide, capryl methyl glucamide, cocoyl methyl glucamide, capryloyl/caproyl methyl glucamide, cocoyl methyl glucamide, lauryl methylglucamide, oleoyl methylglucamide oleate, stearoyl methylglucamide stearate, sunfloweroyl methylglucamide, and tocopheryl succinate methylglucamide.

(ii) Alkyl Polyglucosides

For the purposes of the present invention, the term "alkylpolyglycoside" means an alkylmonosaccharide (degree of polymerization 1) or an alkylpolyglycoside (degree of polymerization greater than 1).

The alkylpolyglycosides may be used alone or in the form of mixtures of several alkylpolyglycosides. Examples of alkyl polyglucosides include those having the following formula:

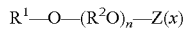

$$R^1\text{—O—}(R^2O)_n\text{—}Z(x)$$

wherein, $R^1$ is an alkyl group having 8-22 carbon atoms;
$R^2$ is an ethylene or propylene group;
Z is a saccharide group with 5 to 6 carbon atoms;
n is an integer from 0 to 10; and
x is an integer from 1 to 5, preferably from 1.05 to 2.5 and more preferentially from 1.1 to 2.

Non-limiting examples of alkyl polyglucosides that may be useful in the hair care compositions include lauryl glucoside, octyl glucoside, decyl glucoside, coco glucoside, caprylyl/capryl glucoside, and sodium lauryl glucose carboxylate. Typically, the at least one alkyl poly glucoside compound is selected from the group consisting of lauryl glucoside, decyl glucoside and coco glucoside. In some instances, the nonionic surfactant is decyl glucoside.

The saccharide residue may be chosen from glucose, dextrose, saccharose, fructose, galactose, maltose, maltotriose, lactose, cellobiose, mannose, ribose, dextran, talose, allose, xylose, levoglucan, cellulose and starch.

More preferentially, the saccharide residue denotes glucose.

It should also be noted that each unit of the polysaccharide part of the alkylpolyglycoside may be in a or beta isomer form, in L or D form, and the configuration of the saccharide residue may be of furanoside or pyranoside type.

It is, of course, possible to use mixtures of alkylpolysaccharides, which may differ from each other in the nature of the borne alkyl unit and/or the nature of the bearing polysaccharide chain.

Alkylpolyglucosides can be also selected from the group consisting of myristyl alcohol/myristyl glucoside (MONTANOV 14); isostearyl alcohol/isostearyl glucoside; cetylstearyl alcohol/cetylstearyl glucoside (MONTANOV 68); cetylstearyl alcohol/coco-glucoside (MONTANOV 82); arachidyl alcohol and behenyl alcohol/arachidyl glucoside (Montanov 202); C14-22 Alcohols/C12-20 Alkyl Glucoside (MONTANOV L); cocoyl alcohol/cocoyl glucoside (MONTANOV S); hydroxystearyl alcohol and hydroxystearyl glucoside (SIMULGREEN 18-2), or any mixture thereof.

In one embodiment, said alkylpolyglucosides are selected from the group consisting of alkylpolyglucosides with an alkyl having from 12 to 22 carbon atoms.

In one embodiment, said alkylpolyglucosides are selected from the group consisting of alkylpolyglucosides with an alkyl having from 14 to 18 carbon atoms.

In one embodiment, said alkylpolyglucosides are present in the form of a mixture of alkylpolysaccharides with an alkyl part having a 12 to 22 carbon atoms and even more preferentially from 12 to 20 carbon atoms.

In one embodiment, said alkylpolyglucosides are selected from the group consisting of caprylyl/capryl glucoside, palmkernel/coco glucoside, cetearyl glucoside, decyl glucoside, lauryl glucoside, coco-glucoside, arachidyl gludoside, C12-20 alkyl glucoside, C10-16 alkyl glucoside, myristyl glucoside, myristoyl ethyl glucoside, methyl coco-glucoside, tallowyl ethyl glucoside, undecyl glucoside, octyldodecyl glucoside, isostearyl glucoside, lauroyl ethyl gludoside, cocoyl ethyl glucoside, caproyl ethyl glucoside, butyl glucoside, or mixtures thereof.

(iii) Miscellaneous Nonionic Surfactants

Nonionic surfactants also include, for example, alcohols, alpha-diols, alkylphenols and esters of fatty acids, being ethoxylated, propoxylated or glycerolated and having at least one fatty chain comprising, e.g., from 8 to 18 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, e.g., from 2 to 30 mole of ethylene oxide; polyglycerolated fatty amides comprising, e.g., from 1.5 to 5 glycerol groups, such as from 1.5 to 4; ethoxylated fatty acid esters of sorbitan comprising from 2 to 30 mole of ethylene oxide; ethoxylated oils from plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and mixtures thereof. In some instances, the nonionic surfactant is chosen from polyoxyalkylenated or polyglycerolated nonionic surfactants. The oxyalkylene units are more particularly oxyethylene or oxypropylene units, or a combination thereof, and are preferably oxyethylene units.

Additionally or alternatively, the nonionic surfactant may be selected from esters of polyols with fatty acids with a saturated or unsaturated chain containing, e.g., from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; polyethylene glycol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sorbitol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sugar (sucrose, glucose, alkylglycose) esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; ethers of fatty alcohols; ethers of sugar and a $C_8$-$C_{24}$, preferably $C_{12}$-$C_{22}$, fatty alcohol or alcohols; and mixtures thereof.

Examples of ethoxylated fatty esters that may be mentioned include the adducts of ethylene oxide with esters of lauric acid, palmitic acid, stearic acid or behenic acid, and mixtures thereof, especially those containing from 9 to 100 oxyethylene groups, such as PEG-9 to PEG-50 laurate (as the CTFA names: PEG-9 laurate to PEG-50 laurate); PEG-9 to PEG-50 palmitate (as the CTFA names: PEG-9 palmitate to PEG-50 palmitate); PEG-9 to PEG-50 stearate (as the CTFA names: PEG-9 stearate to PEG-50 stearate); PEG-9 to PEG-50 palmitostearate; PEG-9 to PEG-50 behenate (as the CTFA names: PEG-9 behenate to PEG-50 behenate); polyethylene glycol 100 EO monostearate (CTFA name: PEG-100 stearate); and mixtures thereof.

The nonionic surfactant may be chosen from glyceryl esters of fatty acids, such as glyceryl stearate (glyceryl mono-, di- and/or tristearate) (CTFA name: glyceryl stearate), glyceryl ricinoleate, and mixtures thereof. The glyceryl esters of fatty acids may be glyceryl esters of $C_8$-$C_{24}$ alkoxylated fatty acids and/or polyethoxylated glyceryl stearate (glyceryl mono-, di- and/or tristearate), such as PEG-20 glyceryl stearate.

Fatty Alcohol(s)

The hair care compositions include one or more fatty alcohols. Preferably, the total amount of fatty alcohols present in the hair care composition is about 0.5 to about 10 wt. %, about 0.5 to about 8 wt. %, about 0.5 to about 6 wt. %, about 0.5 to about 5 wt. %, about 0.5 to about 4 wt. %, about 0.5 to about 3 wt. %, about 0.5 to about 2 wt. %; about 1 to about 10 wt. %, about 1 to about 8 wt. %, about 1 to about 6 wt. %, about 1 to about 5 wt. %, about 1 to about 4 wt. %, about 1 to about 3 wt. %; about 2 to about 10 wt. %, about 2 to about 8 wt. %, about 2 to about 6 wt. %, about 2 to about 5 wt. %, about 2 to about 4 wt. %; about 3 to about 10 wt. %, about 3 to about 8 wt. %, about 3 to about 6 wt. %, or about 3 to about 5 wt. %, including any ranges and subranges therebetween, based on the total weight of the hair care composition.

The hair care compositions may be formulated to have $C_{14-22}$ alcohols in an amount of about 0.05 to about 8 wt. %, about 0.05 to about 6 wt. %, about 0.05 to about 4 wt. %, about 0.05 to about 3 wt. %, about 0.05 to about 2 wt. %, about 0.05 to about 1 wt. %; about 0.1 to about 8 wt. %, about 0.1 to about 6 wt. %, about 0.1 to about 4 wt. %, about 0.1 to about 3 wt. %, about 0.1 to about 2 wt. %, about 0.1 to about 1 wt. %; about 0.5 to about 8 wt. %, about 0.5 to about 6 wt. %, about 0.5 to about 4 wt. %, about 0.5 to about 3 wt. %, about 0.5 to about 2 wt. %, including ranges and subranges therebetween, based on the total weight of the hair care composition.

The hair care composition may include one or more fatty alcohol(s) in addition to $C_{14-22}$ alcohols. For example, the hair care composition may include fatty alcohol(s) having a fatty group with a carbon chain of greater than 8 carbon atoms, 8 to 50 carbon atoms, 8 to 40 carbon atoms, 8 to 30 carbon atoms, 8 to 22 carbon atoms, 12 to 22 carbon atoms, or 12 to 18 carbon atoms, including all ranges and subranges therebetween. In some instances, the fatty group of the fatty alcohols has a carbon chain of 10 to 20 carbon atoms or 10 to 18 carbon atoms. The fatty alcohols may be chosen from polyethylene glycol ethers, such as those having a fatty alcohol group with a carbon chain of 12 to 16 or 12 to 14 carbon atoms. In at least one embodiment, the hair care composition includes octyldodecanol in addition to the $C_{14-22}$ alcohols.

The fatty alcohol portion is preferably hydrogenated (for example, stearyl, lauryl, cetyl, cetearyl); however, the fatty alcohol may contain one or more double bonds (for example, oleyl). Non-limiting examples of fatty alcohols include decyl alcohol, undecyl alcohol, dodecyl alcohol, myristyl alcohol, lauryl alcohol, cetyl alcohol, stearyl alcohol, cetearyl alcohol (cetyl alcohol and stearyl alcohol), isostearyl alcohol, isocetyl alcohol, behenyl alcohol, linalool, oleyl alcohol, cis-4-t-butylcyclohexanol, isotridecyl alcohol, myricyl alcohol, and a mixture thereof. In some cases, the fatty alcohols comprise at least one of or may be chosen from myristyl alcohol, lauryl alcohol, cetyl alcohol, stearyl alcohol, cetearyl alcohol, isostearyl alcohol, oleyl alcohol, isotridecyl alcohol, and a mixture thereof.

The fatty alcohol may be saturated or unsaturated. Exemplary saturated liquid fatty alcohols may be branched and optionally contain in their structure at least one aromatic or non-aromatic ring. In some instances, however, the fatty alcohols are acyclic. Non-limiting examples of liquid saturated fatty alcohols include octyldodecanol, isostearyl alcohol, and 2-hexyldecanol.

Exemplary unsaturated liquid fatty alcohol may include in their structure at least one double or triple bond. For example, the fatty alcohols may include several double bonds (such as 2 or 3 double bond), which may be conjugated or non-conjugated. The unsaturated fatty alcohols can be linear or branched and may be acyclic or include in their structure at least one aromatic or non-aromatic ring. Liquid unsaturated fatty alcohols may include or be chosen from oleyl alcohol, linoleyl alcohol, linolenyl alcohol and undecylenyl alcohol.

The fatty alcohols may be alkoxylated fatty alcohols, e.g., having about 1 to about 100 moles of an alkylene oxide per mole of alkoxylated fatty alcohol. For example, the alkoxylated fatty alcohols may be alkoxylated with about 1 to about 80 moles, about 2 to about 50, about 5 to about 45 moles, about 10 to about 40 moles, or 15 to about 35 mores, including all ranges and subranges therebetween, of an alkylene oxide per mole of alkoxylated fatty alcohol.

As examples of alkoxylated fatty alcohols, steareth (for example, steareth-2, steareth-20, and steareth-21), laureth (for example, laureth-4, and laureth-12), ceteth (for example, ceteth-10 and ceteth-20) and ceteareth (for example, ceteareth-2, ceteareth-10, and ceteareth-20) are mentioned. In at least one instance, the one or more alkoxylated fatty alcohols include steareth-20. In some instances, the one or more alkoxylated fatty alcohols may be exclusively steareth-20.

Additional fatty alcohol derivatives that may, optionally be suitable include methyl stearyl ether; 2-ethylhexyl dodecyl ether; stearyl acetate; cetyl propionate; the ceteth series of compounds, such as ceteth-1 through ceteth-45, which are ethylene glycol ethers of cetyl alcochol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof.

Fatty Ester(s)

The hair care composition includes one or more fatty esters comprising caprylic/capric triglyceride. The total amount of fatty esters present in the hair care composition may be about 1 to about 20 wt. %, based on the total weight of the hair care composition. For instance, the amount of fatty esters in the hair care composition may be about 1 to about 20 wt. %, about 1 to about 18 wt. %, about 1 to about 16 wt. %, about 1 to about 14 wt. %, about 1 to about 12 wt.

%, about 1 to about 11 wt. %, about 1 to about 10 wt. %, about 1 to about 9 wt. %; about 3 to about 20 wt. %, about 3 to about 18 wt. %, about 3 to about 16 wt. %, about 3 to about 14 wt. %, about 3 to about 12 wt. %, about 3 to about 11 wt. %, about 3 to about 10 wt. %, about 3 to about 9 wt. %; about 5 to about 20 wt. %, about 5 to about 18 wt. %, about 5 to about 16 wt. %, about 5 to about 14 wt. %, about 5 to about 12 wt. %, about 5 to about 11 wt. %, about 5 to about 10 wt. %, or about 5 to about 9 wt. %, including ranges and subranges therebetween, based on the total weight of the hair care composition.

The hair care compositions may include caprylic/capric triglyceride in an amount of about 0.01 to about 8 wt. %, about 0.01 to about 6 wt. %, about 0.01 to about 4 wt. %, about 0.01 to about 3 wt. %, about 0.01 to about 2 wt. %, about 0.01 to about 1 wt. %; about 0.05 to about 8 wt. %, about 0.05 to about 6 wt. %, about 0.05 to about 4 wt. %, about 0.05 to about 3 wt. %, about 0.05 to about 2 wt. %, about 0.05 to about 1 wt. %; about 0.1 to about 8 wt. %, about 0.1 to about 6 wt. %, about 0.1 to about 4 wt. %, about 0.1 to about 3 wt. %, about 0.1 to about 2 wt. %, about 0.1 to about 1 wt. %; about 0.5 to about 8 wt. %, about 0.5 to about 6 wt. %, about 0.5 to about 4 wt. %, about 0.5 to about 3 wt. %, about 0.5 to about 2 wt. %, including ranges and subranges therebetween, based on the total weight of the hair care composition.

The hair care composition preferably include one or more fatty esters in addition to caprylic/capric triglyceride. For example, the fatty ester(s) may be chosen from from dialkyl carbonates of formula: $R_1O(C=O)R_2$, wherein $R_1$ and $R_2$ are independently linear or branched, saturated or unsaturated alkyl chains having 1 to 30 carbon atoms, or having 2 to 28 carbon atoms, or having 4 to 25 carbon atoms, or having 6 to 22 carbon atoms, preferably one or more fatty carbonates selected from C14-15 dialkyl carbonate, dicaprylyl carbonate, diethyl carbonate, dihexyl carbonate, diethylhexyl carbonate, dimethoxyphenyl phenyloxoethyl ethylcarbonate, dimethyl carbonate, dipropyl carbonate, dipropylheptyl carbonate, dioctyl carbonate, and a mixture thereof. In at least one instance, the hair care composition comprises isopropyl myristate and glyceryl stearate in addition to caprylic/capric triglyceride.

Additionally or alternatively, the fatty ester may be chosen from cetyl ester, purcellin oil (cetearyl octanoate), isopropyl myristate, isopropyl palmitate, glyceryl stearate, $C_{12}$-$C_{15}$ alkyl benzoate, 2-ethylphenyl benzoate, isopropyl lanolate, hexyl laurate, diisopropyl adipate, isononyl isononanoate, oleyl erucate, 2-ethylhexyl palmitate, isostearyl isostearate, diisopropyl sebacate, octanoates, decanoates or ricinoleates of alcohols or polyalcohols, hydroxylated esters, dicaprylyl carbonate, pentaerythritol esters, and a mixture thereof. Other fatty esters worth mentioning include polyglyceryl-10 oleate, polyglyceryl-10 dioleate, polyglyceryl-6 stearate, polyglyceryl-6 distearate, polyglyceryl-10 stearate, polyglyceryl-10 distearate, polyglyceryl-8 dipalmitate, polyglyceryl-10 dipalmitate, polyglyceryl-10 behenate, and polyglyceryl-12 trilaurate.

Fatty Compound(s) Other than Fatty Alcohol and Fatty Ester

The hair care compositions include one or more fatty compounds other than fatty alcohol and fatty ester in an amount typically ranging from about 0.5 to about 30 wt. %, based on the total weight of the hair care compositions. In some instances, the total amount of fatty compounds other than fatty alcohol and fatty ester present in the hair care composition is about 0.5 to about 30 wt. %, about 0.5 to about 25 wt. %, about 0.5 to about 20 wt. %, about 0.5 to about 25 wt. %, about 0.5 to about 20 wt. %, about 0.5 to about 15 wt. %, about 0.5 to about 12.5 wt. %, about 0.5 to about 10 wt. %, about 0.5 to about 8 wt. %; about 2 to about 30 wt. %, about 2 to about 25 wt. %, about 2 to about 20 wt. %, about 2 to about 25 wt. %, about 2 to about 20 wt. %, about 2 to about 15 wt. %, about 2 to about 12.5 wt. %, about 2 to about 10 wt. %, about 2 to about 8 wt. %; about 5 to about 30 wt. %, about 5 to about 25 wt. %, about 5 to about 20 wt. %, about 5 to about 25 wt. %, about 5 to about 20 wt. %, about 5 to about 15 wt. %, about 5 to about 12.5 wt. %, about 5 to about 10 wt. %, about 5 to about 8 wt. %; about 7 to about 30 wt. %, about 7 to about 25 wt. %, about 7 to about 20 wt. %, about 7 to about 25 wt. %, about 7 to about 20 wt. %, about 7 to about 15 wt. %, about 7 to about 12.5 wt. %, or about 7 to about 10 wt. %, including ranges and subranges therebetween, based on the total weight of the hair care composition.

Fatty Ether(s)

The hair care compositions may, optionally, include one or more fatty ethers. The total amount of fatty ethers if present in the hair care composition may be about 0.05 to about 8 wt. %, about 0.05 to about 6 wt. %, about 0.05 to about 4 wt. %, about 0.05 to about 3 wt. %, about 0.05 to about 2 wt. %, about 0.05 to about 1 wt. %; about 0.1 to about 8 wt. %, about 0.1 to about 6 wt. %, about 0.1 to about 4 wt. %, about 0.1 to about 3 wt. %, about 0.1 to about 2 wt. %, about 0.1 to about 1 wt. %; about 0.5 to about 8 wt. %, about 0.5 to about 6 wt. %, about 0.5 to about 4 wt. %, about 0.5 to about 3 wt. %, about 0.5 to about 2 wt. %; about 1 to about 8 wt. %, about 1 to about 6 wt. %, about 1 to about 5 wt. %, about 1 to about 4 wt. %, about 1 to about 3 wt. %; about 2 to about 8 wt. %, about 2 to about 6 wt. %, about 2 to about 5 wt. %, about 2 to about 4 wt. %; about 3 to about 8 wt. %, about 3 to about 6 wt. %, about 3 to about 5 wt. %, including ranges and subranges therebetween, based on the total weight of the hair care composition.

The fatty ethers may be chosen from olyoxyethylene cetyl/stearyl ether, polyoxyethylene cholesterol ether, polyoxyethylene laurate or dilaurate, polyoxyethylene stearate or distearate, polyoxyethylene lauryl or stearyl ether, dicaprylyl ether, dicetyl ether distearyl ether, and a mixture thereof. Non-limiting examples of suitable polyoxyethylene fatty ethers include, but are not limited to, polyoxyethylene cetyl/stearyl ether, polyoxyethylene cholesterol ether, polyoxyethylene laurate or dilaurate, polyoxyethylene stearate or distearate, polyoxyethylene lauryl or stearyl ether, and mixtures thereof, wherein the polyoxyethylene head group ranges from about 2 to about 100 groups. In certain embodiments, the polyoxyethylene fatty ethers include polyoxyethylene stearyl ether, polyoxyethylene myristyl ether, polyoxyethylene lauryl ether having from about 3 to about 10 oxyethylene units and mixtures thereof.

Fatty Acid(s)

In some cases, the hair care compositions may include one or more fatty acids. The total amount of fatty acids if present in the hair care composition may be about 0.05 to about 8 wt. %, about 0.05 to about 6 wt. %, about 0.05 to about 4 wt. %, about 0.05 to about 3 wt. %, about 0.05 to about 2 wt. %, about 0.05 to about 1 wt. %; about 0.1 to about 8 wt. %, about 0.1 to about 6 wt. %, about 0.1 to about 4 wt. %, about 0.1 to about 3 wt. %, about 0.1 to about 2 wt. %, about 0.1 to about 1 wt. %; about 0.5 to about 8 wt. %, about 0.5 to about 6 wt. %, about 0.5 to about 4 wt. %, about 0.5 to about 3 wt. %, about 0.5 to about 2 wt. %; about 1 to about 8 wt. %, about 1 to about 6 wt. %, about 1 to about 5 wt. %, about 1 to about 4 wt. %, about 1 to about 3 wt. %; about 2 to about 8 wt. %, about 2 to about 6 wt. %, about 2 to about 5 wt. %, about 2 to about 4 wt. %; about 3 to about 8 wt. %, about 3 to about 6 wt. %, about 3 to about 5 wt. %, including ranges and subranges therebetween, based on the total weight of the hair care composition.

The hair care compositions may include one or more fatty acids, fatty acid derivatives, esters of fatty acids, hydroxyl-substituted fatty acids, and alkoxylated fatty acids. The fatty acids may be straight or branched chain acids and/or may be saturated or unsaturated. Non-limiting examples of fatty acids include diacids, triacids, and other multiple acids as well as salts of these fatty acids. For example, the fatty acid may optionally include or be chosen from lauric acid, palmitic acid, stearic acid, behenic acid, arichidonic acid, oleic acid, isostearic acid, sebacic acid, and a mixture thereof. In some cases, the fatty acids are selected from the group consisting of palmitic acid, stearic acid, and a mixture thereof.

Non-limiting examples of polyglycerol esters of fatty acids include those of the following formula:

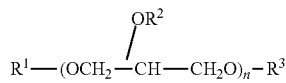

wherein the average value of n is about 3 and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$.

The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substituted fatty acids, and a mixture thereof. Non-limiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof. Preferred for use herein are glycerol monostearate, 12-hydroxy stearic acid, and a mixture thereof.

Wax(es)

The hair care compositions may, in some instances, include one or more waxes. The total amount of fatty acids if present in the hair care composition may be about 0.5 to about 8 wt. %, about 0.5 to about 6 wt. %, about 0.5 to about 4 wt. %, about 0.5 to about 3 wt. %, about 0.5 to about 2 wt. %; about 1 to about 8 wt. %, about 1 to about 6 wt. %, about 1 to about 5 wt. %, about 1 to about 4 wt. %, about 1 to about 3 wt. %; about 2 to about 8 wt. %, about 2 to about 6 wt. %, about 2 to about 5 wt. %, about 2 to about 4 wt. %; about 3 to about 8 wt. %, about 3 to about 6 wt. %, about 3 to about 5 wt. %, including ranges and subranges therebetween, based on the total weight of the hair care composition.

Non-limiting examples of waxes in this category include for example, synthetic wax, ceresin, paraffin, ozokerite, polyethylene waxes, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, acacia decurrents flower wax, vegetable waxes (such as sunflower seed (*Helianthus annuus*), carnauba, candelilla, ouricury or japan wax or cork fibre or sugarcane waxes), or a mixture thereof. The hair care compositions may include two or more waxes, such as two or more waxes selected from those mentioned above. In one embodiment, the hair care composition includes butyrospermum parkii (shea) butter, euphorbia cerifera (candelilla) wax, and beeswax.

Other Fatty Compounds(s)

The hair care compositions include fatty compounds other than those mentioned above. Generally, the following fatty compounds are considered oil(s). As noted above, the total amount of oil may include oils that are fatty alcohols, fatty esters, fatty ethers, fatty acids, silicones and/or the like. The total amount of oil may be about 1 to about 20 wt. %, based on the total weight of the hair care composition. In some cases, the total amount of oil chosen fatty compounds and silicones may be about 1 to about 20 wt. %, about 2 to about 20 wt. %, about 3 to about 20 wt. %, about 4 to about 20 wt. %, about 5 to about 20 wt. %, about 6 to about 20 wt. %, about 8 to about 20 wt. %, about 10 to about 20 wt. %, about 12.5 to about 20 wt. %, about 15 to about 20 wt. %; about 1 to about 18 wt. %, about 2 to about 18 wt. %, about 3 to about 18 wt. %, about 4 to about 18 wt. %, about 5 to about 18 wt. %, about 6 to about 18 wt. %, about 8 to about 18 wt. %, about 10 to about 18 wt. %, about 12.5 to about 18 wt. %, about 15 to about 18 wt. %; about 1 to about 16 wt. %, about 2 to about 16 wt. %, about 3 to about 16 wt. %, about 4 to about 16 wt. %, about 5 to about 16 wt. %, about 6 to about 16 wt. %, about 8 to about 16 wt. %, about 10 to about 16 wt. %, about 12.5 to about 16 wt. %, about 15 to about 16 wt. %, including any ranges and subranges therebetween, based on the total weight of the hair care composition.

Non-limiting examples of fatty compounds that are oils include, but are not limited to, natural fatty oils, such as coconut oil; hydrocarbons, such as mineral oil and hydrogenated polyisobutene; esters, such as $C_{12}$-$C_{15}$ alkyl benzoate; diesters, such as propylene dipelarganate; and triesters, such as glyceryl trioctanoate. Further examples of fatty compounds that are oils include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or combinations of octyldodecanol, acetylated lanolin alcohol, cetyl acetate, isododecanol, polyglyceryl-3-diisostearate, castor oil, lanolin and lanolin derivatives, triisocetyl citrate, sorbitan sesquioleate, $C_{10}$-$C_{18}$ triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or combinations thereof.

Additionally or alternatively, fatty compounds, which are oils, may be selected from plant based and/or vegetable oils. Non-limiting examples of plant-based or vegetable oils include acai oil, almond oil, aloe vera oil, andiroba oil, annatto oil, avocado oil, babassu oil, borage oil, brazil nut oil, buriti oil, camelina oil, coffee oil, copaiba oil, emu oil, passion fruit oil, almond oil, *Ricinus communis* (castor) seed oil, coconut oil, grapeseed oil, jojoba oil, macadamia nut oil, rose hip oil, ajwain oil, angelic root oil, anise oil, aragan oil, asafetida, balsam oil, basil oil, bay oil, bergamot oil, black pepper essential oil, buchu oil, birch oil, camphor, cannabis oil, caraway oil, cardamom seed oil, carrot seed oil, chamomile oil, calamus root oil, cinnamon oil, citronella oil, clary sage, clove leaf oil, coffee, coriander, costmary oil, cranberry seed oil, cubeb, cumin oil, cypress, cypriol, curry leaf, davana oil, dill oil, elecampane, eucalyptus oil, fennel seed oil, fenugreek oil, fir, frankincense oil, galangal, geranium oil, ginger oil, goldenrod, grapefruit oil, grapeseed oil, henna oil, helichrysum, horseradish oil, hyssop, Idaho tansy, jasmine oil, juniper berry oil, lavender oil, lemon oil, lemongrass, marjoram, melaleuca, lemon balm oil, mountain savory, mugwort oil, mustard oil, myrrh oil, myrtle, neem tree oil, neroli, nutmeg, orange oil, oregano oil, orris oil, palo santo, parsley oil, patchouli oil, perilla oil, pennyroyal oil, peppermint oil, petitgrain, pine oil, plum oil, ravensara, red cedar, roman chamomile, rose oil, rosehip oil, rosemary oil, rosewood oil, sandalwood oil, sassafras oil, savory oil, schisandra oil, spikenard, spruce, star anise oil, tangerine, tarragon oil, tea tree oil, thyme oil, tsuga oil, turmeric, valerian, vetiver oil, western red cedar, wintergreen, yarrow oil, ylang-ylang, and zedoary oil.

Non-limiting examples of fatty oils of plant origin include alexandria laurel tree oil, avocado oil, apricot stone oil, barley oil, borage seed oil, calendula oil, canelle nut tree oil, canola oil, caprylic/capric triglyceride castor oil, coconut oil, corn oil, cotton oil, cottonseed oil, evening primrose oil, flaxseed oil, groundnut oil, hazelnut oil, glycereth triacetate, glycerol triheptanoate, glyceryl trioctanoate, glyceryl triundecanoate, hempseed oil, jojoba oil, lucerne oil, maize germ oil, marrow oil, millet oil, neopentylglycol dicaprylate/dicaprate, olive oil, palm oil, passionflower oil, pentaerythrityl tetrastearate, poppy oil, propylene glycol ricinoleate, rapeseed oil, rye oil, safflower oil, sesame oil, shea butter, soya oil, soybean oil, sweet almond oil, sunflower oil, sysymbrium oil, syzigium aromaticum oil, tea tree oil, walnut oil, wheat germ glycerides and wheat germ oil.

Silicone(s)

The hair care compositions include one or more silicone(s) comprising polysilicone-11. Polysilicone-11 is commercially available as a blend with dimethicone under the tradename of GRANSIL DMG-6LC from the company Grant Industries.

The total amount of silicone(s) present in the hair care composition may be from about 0.5 to about 10 wt. %, based on the total weight of the hair care composition. For example, the total amount of silicone(s) present in the hair care composition may be about 0.5 to about 10 wt. %, about 0.5 to about 8 wt. %, about 0.5 to about 6 wt. %, about 0.5 to about 5 wt. %, about 0.5 to about 4 wt. %, about 0.5 to about 3 wt. %, about 0.5 to about 2 wt. %; about 1 to about 10 wt. %, about 1 to about 8 wt. %, about 1 to about 6 wt. %, about 1 to about 5 wt. %, about 1 to about 4 wt. %, about 1 to about 3 wt. %; about 2 to about 10 wt. %, about 2 to about 8 wt. %, about 2 to about 6 wt. %, about 2 to about 5 wt. %, about 2 to about 4 wt. %; about 3 to about 10 wt. %, about 3 to about 8 wt. %, about 3 to about 6 wt. %, or about 3 to about 5 wt. %, including any ranges and subranges therebetween, based on the total weight of the hair care composition.

The hair care compositions may include one or more silicones in addition to polysilicone-11. The silicones may, optionally, be functionalized with an amino group or functionalized with a methacrylic group. The term "amino-functionalized silicone" or "amino silicones" means a silicone containing at least one primary amino, secondary amino, tertiary amino and/or quaternary ammonium group. The structure of the amino-functionalized silicone may be linear or branched, cyclic or non-cyclic. The amino functional group may be at any position in the silicone molecule, preferably at the end of the backbone (for example, in the case of amodimethicones) and/or in the side chain.

Non-limiting examples of silicones include amine-functionalized silicones (e.g., amodimethicone), dimethicone, bis-aminopropyl dimethicone, trimethyl silylamodimethicone, dimethicone copolyols, etc. The hair care composition may include, in some instances, one or more silicones chosen from polydimethylsiloxanes (dimethicones), polydiethylsiloxanes, polydimethyl siloxanes having terminal hydroxyl groups (dimethiconols), polymethylphenylsiloxanes, phenylmethylsiloxanes, amino functional polydimethylsiloxane (amodimethicone), bis-aminopropyl dimethicone, trimethylsilylamodimethicone, dimethicone copolyols, dimethicone copolyol esters, dimethicone copolyol quaternium nitrogen containing compounds, dimethicone copolyol phosphate esters, and mixtures thereof. For example, the one or more silicones may be or include one or more dimethicone copolyols. The copolyols may be chosen from Dimethicone PEG-8 Adipate, Dimethicone PEG-8 Benzoate, Dimethicone PEG-7 Phosphate, Dimethicone PEG-10 Phosphate, Dimethicone PEG/PPG-20/23 Benzoate, Dimethicone PEG/PPG-7/4 Phosphate, Dimethicone PEG/PPG-12/4 Phosphate, PEG-3 Dimethicone, PEG-7 Dimethicone, PEG-8 Dimethicone, PEG-9 Dimethicone, PEG-10 Dimethicone, PEG-12 Dimethicone, PEG-14 Dimethicone, PEG-17 Dimethicone, PEG/PPG-3/10 Dimethicone, PEG/PPG-4/12 Dimethicone, PEG/PPG-6/11 Dimethicone, PEG/PPG-8/14 Dimethicone, PEG/PPG-14/4 Dimethicone, PEG/PPG-15/15 Dimethicone, PEG/PPG-16/2 Dimethicone, PEG/PPG-17/18 Dimethicone, PEG/PPG-18/18 Dimethicone, PEG/PPG-19/19 Dimethicone, PEG/PPG-20/6 Dimethicone, PEG/PPG-20/15 Dimethicone, PEG/PPG-20/20 Dimethicone, PEG/PPG-20/23 Dimethicone, PEG/PPG-20/29 Dimethicone, PEG/PPG-22/23 Dimethicone, PEG/PPG-22/24 Dimethicone, PEG/PPG-23/6 Dimethicone, PEG/PPG-25/25 Dimethicone, PEG/PPG-27/27 Dimethicone, and a mixture thereof.

The silicone(s) may, optionally, include or be chosen from a siloxane with a methacrylic group on one of its molecular ends, polydimethylsiloxane containing a styryl group on one of its molecular ends, or a similar silicone compound containing unsaturated groups; butadiene; vinyl chloride; vinylidene chloride; methacrylonitrile; dibutyl fumarate; anhydrous maleic acid; anhydrous succinic acid; methacryl glycidyl ether; an organic salt of an amine, an ammonium salt, and an alkali metal salt of methacrylic acid, of itaconic acid, of crotonic acid, of maleic acid or of fumaric acid; a radical-polymerizable unsaturated monomer containing a sulfonic acid group such as a styrenesulfonic acid group; a quaternary ammonium salt derived from methacrylic acid, such as 2-hydroxy-3-methacryloxypropyltrimethylammonium chloride; and a methacrylic acid ester of an alcohol containing a tertiary amine group, such as a methacrylic acid ester of diethylamine.

One or more silicone(s) may be included in the hair care composition has an emulsifier. For example, the silicone may be an organosiloxane emulsifier, oxyalkylenated organosiloxane emulsifier, PEGylated organic siloxane emulsifiers, or a cross-linked organosiloxane emulsifiers. Although not specifically identified, some of the silicones listed below may be utilized as emulsifiers.

In some cases, the silicones, optionally, include or are chosen from siloxanes having an organo functional group, such as polyalkylsiloxanes, where at least one alkyl radical is different than methyl, for example organopolysiloxanes having the INCI name Stearyl Dimethicone, Cetyl Dimethicone or C26-28 Alkyl Dimethicone, or, for example, polyarylsiloxanes and polyarylalkylsiloxanes, for example organopolysiloxanes having the INCI name Phenyl Trimethicone, Trimethylsiloxyphenyl Dimethicone or Dimethylphenyl Dimethicone, or, for example, organopolysiloxanes having an organofunctional radical such as an aminopropyl, aminopropyl-aminoethyl, aminopropyl-aminoisobutyl radical, for example organopolysiloxanes having the INCI name Amodimethicone, or, for example, organopolysiloxanes having a polyethylene glycol or polyalkylene glycol radical, for example organopolysiloxanes having the INCI name PEG-12 Dimethicone, PEG/PPG-25,25-Dimethicone or Cetyl PEG/PPG-15/15 Butyl Ether Dimethicone.

In some instances, an amino-functionalized silicones is selected from compounds having the following formula:

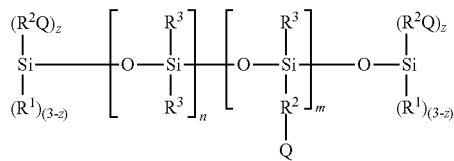

wherein each $R^1$ is independently selected from a $C_{1-30}$ alkyl group, a $C_{1-30}$ alkoxy group, a $C_{5-30}$ aryl group, a $C_{6-30}$ aralkyl group, a $C_{6-30}$ aralkyloxy group, a $C_{1-30}$ alkaryl group, a $C_{1-30}$ alkoxyaryl group, and a hydroxy group (preferably, each $R^1$ is independently selected from a $C_{1-30}$ alkyl group, a $C_{1-30}$ alkoxy group and a hydroxy group);

each $R^2$ is independently a divalent alkylene radical having one to ten carbon atoms (preferably, $R^2$ is a divalent alkylene radical having three to six carbon atoms);

each $R^3$ is independently selected from a $C_{1-30}$ alkyl group, a $C_{5-30}$ aryl group, a $C_{6-30}$ aralkyl group and a $C_{1-30}$ alkaryl group (preferably, each $R^3$ is independently selected from of a $C_{1-30}$ alkyl group);

Q is a monovalent radical selected from $-NR^4_2$ and $-NR^4(CH_2)_xNR^4_2$;

each $R^4$ is independently selected from a hydrogen and a $C_{1-4}$ alkyl group;

x is 2 to 6;

z is 0 or 1;

n is 25 to 3,000 (preferably, 25 to 2,000; more preferably, 25 to 1,000; most preferably 25 to 500); and m is 0 to 3,000 (preferably, 0 to 2,000; more preferably, 0 to 1,000; most preferably 0 to 100);

with the proviso that at least 50 mol % of the total number of $R^1$ and $R^3$ groups are methyl and with the proviso that when m is 0, z is 1.

Preferred $R^1$ groups include methyl, methoxy, ethyl, ethoxy, propyl, propoxy, isopropyl, isopropoxy, butyl, butoxy, isobutoxy, phenyl, xenyl, benzyl, phenylethyl, tolyl and hydoxy. Preferred $R^2$ divalent alkylene radicals include trimethylene, tetramethylene, pentamethylene, $-CH_2CH(CH_3)CH_2-$ and $-CH_2CH_2CH(CH_3)CH_2-$. Preferred $R^3$ groups include methyl, ethyl, propyl, isopropyl, butyl, isobutyl, phenyl, xenyl, benzyl, phenylethyl and tolyl. Preferred $R^4$ groups include methyl, ethyl, propyl, isopropyl, butyl and isobutyl. When z is 0, the amino-functionalized silicine has only pendant amine functional substituents in the polymer chain. When z is 1, the amino-functional silicone may have only terminal amine functional substituents (e.g., m=0) or may have both terminal and pendant amine functional substituents in the polymer chain (e.g., m>0). Preferably, n+m is 50 to 1,000. More preferably, n+m is 50 to 750. Still more preferably, n+m is 50 to 500. Most preferably, n+m is 50 to 250.

In some instances, the amino-functionalized silicones are alkoxylated and/or hydroxylated amino silicones. Suitable alkoxylated and/or hydroxylated amino silicones may be selected from compounds of the following formula:

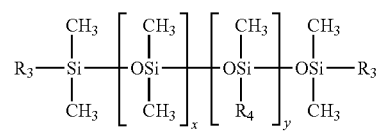

wherein $R_3$ is hydroxyl or $OR_5$, $R_5$ is a $C_1$ to $C_4$ alkyl group, $R_4$ is a group with structure according to the following formula:

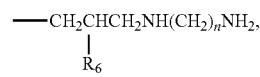

$R_6$ is a $C_1$ to $C_4$ alkyl, n is a 1 to 4, x is the same as "n" described above, and y is the same as "m" described above.

The silicone may be a polysiloxane corresponding to the following formula:

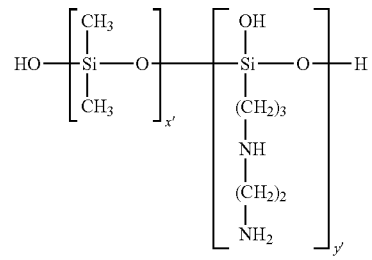

in which x' and y' are integers such that the weight-average molecular weight (Mw) is comprised between about 5000 and 500 000;

b) amino silicones corresponding to following formula:

in which:

G, which may be identical or different, designate a hydrogen atom, or a phenyl, OH or $C_1$-$C_8$ alkyl group, for example methyl, or $C_1$-$C_8$ alkoxy, for example methoxy, a, which may be identical or different, denote the number 0 or an integer from 1 to 3, in particular 0;

b denotes 0 or 1, and in particular 1;

m and n are numbers such that the sum (n+m) ranges from 1 to 2000 and in particular from 50 to 150, it being possible for n to denote a number from 0 to 1999 and in particular from 49 to 149, and form to denote a number from 1 to 2000 and in particular from 1 to 10;

R', which may be identical or different, denote a monovalent radical having formula —CqH$_2$qL in which q is a number ranging from 2 to 8 and L is an optionally quaternized amino group chosen from the following groups:

—NR"-Q-N(R")$_2$

—N(R")$_2$

—N+(R")$_3$ A-

—N+H(R")$_2$ A-

—N+H$_2$(R") A-

—N(R")-Q-N+R"H$_2$ A-

—NR"-Q-N+(R")$_2$H A-

—NR"-Q-N+(R")$_3$ A-, in which R", which may be identical or different, denote hydrogen, phenyl, benzyl, or a saturated monovalent hydrocarbon-based radical, for example a $C_1$-$C_{20}$ alkyl radical; Q denotes a linear or branched $CrH_{2r}$ group, r being an integer ranging from 2 to 6, preferably from 2 to 4; and A- represents a cosmetically acceptable ion, in particular a halide such as fluoride, chloride, bromide or iodide.

Another group of amino silicones corresponding to this definition is represented by silicones having the following formula:

$$R_1-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_n-\left[\underset{\underset{(CH_2)_3-NH-(CH_2)_2-NH_2}{|}}{\overset{\overset{R_2}{|}}{Si}}-O\right]_m-\underset{\underset{CH_3}{|}}{\overset{\overset{CH_3}{|}}{Si}}-R_3$$

in which:

m and n are numbers such that the sum (n+m) can range from 1 to 1000, in particular from 50 to 250 and more particularly from 100 to 200, it being possible for n to denote a number from 0 to 999 and in particular from 49 to 249, and more particularly from 125 to 175, and for m to denote a number from 1 to 1000 and in particular from 1 to 10, and more particularly from 1 to 5;

$R_1$, $R_2$, $R_3$, which may be identical or different, represent a hydroxy or $C_1$-$C_4$ alkoxy radical, where at least one of the radicals $R_1$ to $R_3$ denotes an alkoxy radical.

The alkoxy radical is preferably a methoxy radical. The hydroxy/alkoxy mole ratio ranges preferably from 0.2:1 to 0.4:1 and preferably from 0.25:1 to 0.35:1 and more particularly equals 0.3:1. The weight-average molecular weight (Mw) of the silicone ranges preferably from 2,000 to 1,000,000, more particularly from 3,500 to 200,000.

Another group of amino silicones corresponding to this definition is represented by the following formula:

$$R_1-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_p-\left[\underset{\underset{(CH_2)_3-NH-(CH_2)_2-NH_2}{|}}{\overset{\overset{CH_3}{|}}{Si}}-O\right]_q-\underset{\underset{CH_3}{|}}{\overset{\overset{CH_3}{|}}{Si}}-R_2$$

in which:

p and q are numbers such that the sum (p+q) ranges from 1 to 1000, particularly from 50 to 350, and more particularly from 150 to 250; it being possible for p to denote a number from 0 to 999 and in particular from 49 to 349, and more particularly from 159 to 239 and for q to denote a number from 1 to 1000, in particular from 1 to 10, and more particularly from 1 to 5;

$R_1$, $R_2$, which may be the same or different, represent a hydroxy or $C_1$-$C_4$ alkoxy radical, where at least one of the radicals $R_1$ or $R_2$ denotes an alkoxy radical.

The alkoxy radical is preferably a methoxy radical. The hydroxy/alkoxy mole ratio ranges generally from 1:0.8 to 1:1.1 and preferably from 1:0.9 to 1:1 and more particularly equals 1:0.95.

Another group of amino silicones is represented by the following formula:

$$HO-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_n-\left[\underset{\underset{NH-(CH_2)_2-NH_2}{|}}{\overset{\overset{CH_3}{|}}{Si}}-O\right]_m-\underset{\underset{CH_3}{|}}{\overset{\overset{CH_3}{|}}{Si}}-OH$$

in which:

m and n are numbers such that the sum (n+m) ranges from 1 to 2000 and in particular from 50 to 150, it being possible for n to denote a number from 0 to 1999 and in particular from 49 to 149, and form to denote a number from 1 to 2000 and in particular from 1 to 10;

A denotes a linear or branched alkylene radical containing from 4 to 8 carbon atoms and preferably 4 carbon atoms. This radical is preferably linear. The weight-average molecular weight (Mw) of these amino silicones ranges preferably from 2000 to 1 000 000 and even more particularly from 3500 to 200 000.

Another group of amino silicones is represented by the following formula:

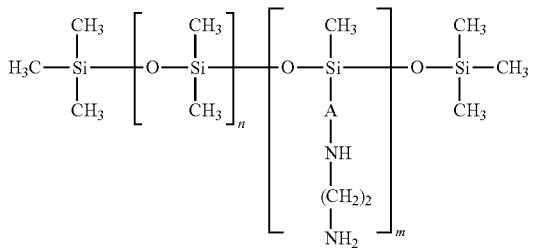

in which:

m and n are numbers such that the sum (n+m) ranges from 1 to 2000 and in particular from 50 to 150, it being possible for n to denote a number from 0 to 1999 and in particular from 49 to 149, and form to denote a number from 1 to 2000 and in particular from 1 to 10;

A denotes a linear or branched alkylene radical containing from 4 to 8 carbon atoms and preferably 4 carbon atoms. This radical is preferably branched. The weight-average molecular weight (Mw) of these amino silicones ranges preferably from 500 to 1 000 000 and even more particularly from 1000 to 200 000.

Another group of amino silicones is represented by the following formula:

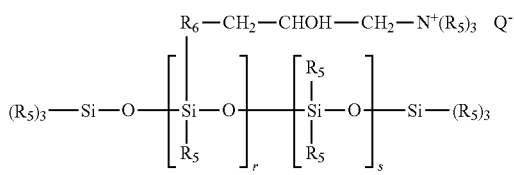

in which:

$R_5$ represents a monovalent hydrocarbon-based radical containing from 1 to 18 carbon atoms, and in particular a $C_1$-$C_{18}$ alkyl or $C_2$-$C_{18}$ alkenyl radical, for example methyl;

$R_6$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;

Q- is an anion such as a halide ion, in particular chloride, or an organic acid salt (for example acetate);

r represents a mean statistical value from 2 to 20 and in particular from 2 to 8;

s represents a mean statistical value from 20 to 200 and in particular from 20 to 50. Such amino silicones are described more particularly in U.S. Pat. No. 4,185,087, which is incorporated herein in its entirety for all purposes.

A group of quaternary ammonium silicones is represented by the following formula:

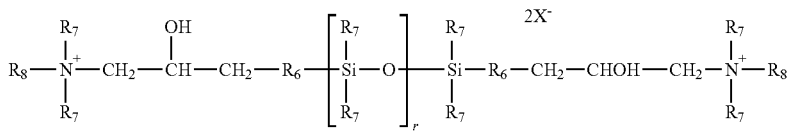

in which:

$R_7$, which may be identical or different, represent a monovalent hydrocarbon-based radical containing from 1 to 18 carbon atoms, and in particular a $C_1$-$C_{18}$ alkyl radical, a $C_2$-$C_{18}$ alkenyl radical or a ring containing 5 or 6 carbon atoms, for example methyl;

$R_6$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;

$R_8$, which may be identical or different, represent a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a —$R_6$—NHCOR$_7$ radical;

X— is an anion such as a halide ion, in particular chloride, or an organic acid salt (for example acetate);

r represents a mean statistical value from 2 to 200 and in particular from 5 to 100. These silicones are described, for example, in European patent application no. 0530974, which is incorporated herein in its entirety for all purposes.

A group of quaternary ammonium silicones is represented by the following formula:

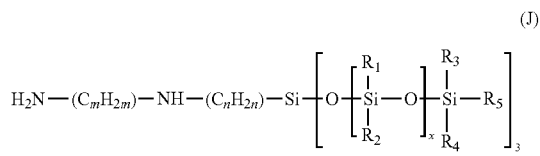

(J)

in which:

$R_1$, $R_2$, $R_3$ and $R_4$, which may be identical or different, denote a $C_1$-$C_4$ alkyl radical or a phenyl group;

$R_5$ denotes a $C_1$-$C_4$ alkyl radical or a hydroxyl group;

n is an integer ranging from 1 to 5;

m is an integer ranging from 1 to 5;

and in which x is chosen such that the amine number is between 0.01 and 1 meq/g;

multiblockpolyoxyalkylenated amino silicones, of type (AB)n, A being a polysiloxane block and B being a polyoxyalkylenated block containing at least one amine group.

Said silicones are preferably constituted of repeating units having the following general formulae:

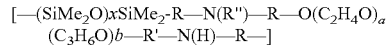

or alternatively

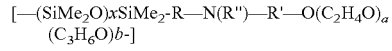

in which:

a is an integer greater than or equal to 1, preferably ranging from 5 to 200, more particularly ranging from 10 to 100;

b is an integer comprised between 0 and 200, preferably ranging from 4 to 100, more particularly between from 5 and 30;

x is an integer ranging from 1 to 10 000, more particularly from 10 to 5000;

R" is a hydrogen atom or a methyl;

R, which may be identical or different, represent a divalent linear or branched $C_2$-$C_{12}$ hydrocarbon-based radical, optionally including one or more heteroatoms such as oxygen; preferably, R denotes an ethylene radical, a linear or branched propylene radical, a linear or branched butylene radical, or a —$CH_2CH_2CH_2OCH(OH)CH_2$— radical; preferentially R denotes a —$CH_2CH_2CH_2OCH(OH)CH_2$— radical;

R', which may be identical or different, represent a divalent linear or branched $C_2$-$C_{12}$ hydrocarbon-based radical, optionally including one or more heteroatoms such as oxygen; preferably, R' denotes an ethylene radical, a linear or branched propylene radical, a linear or branched butylene radical, or a —$CH_2CH_2CH_2OCH(OH)CH_2$— radical; preferentially R' denotes —$CH(CH_3)$—$CH_2$—. The siloxane blocks preferably represent between 50 and 95 mol % of the total weight of the silicone, more particularly from 70 to 85 mol %.

The amine content is preferably between 0.02 and 0.5 meq/g of copolymer in a 30% solution in dipropylene glycol, more particularly between 0.05 and 0.2. The weight-average molecular weight (Mw) of the silicone oil is preferably comprised between 5000 and 1,000,000, more particularly between 10,000 and 200,000.

The silicone may be selected from those having at least one quaternary ammonium group. Suitable non-limiting examples are quaternium 80, silicone quaternium-1, silicone quaternium-2, silicone quaternium-2 panthenol succinate, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-16, silicone quaternium-16/Glycidoxy Dimethicone Crosspolymer, silicone quaternium-17, silicone quaternium-18, silicone quaternium-20 and silicone quaternium-21. Preferred are quaternium 80, silicone quaternium-16, silicone quaternium-18, silicone quaternium-1, silicone quaternium-2, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-17, silicone quaternium-20 and silicone quaternium-21. More preferred are quaternium 80, silicone quaternium-16, silicone quaternium-18, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, and silicone quaternium-17. Preferred are quaternium 80, silicone quaternium-16, silicone quaternium-18, silicone quaternium-15, and mixtures thereof. In an embodiment, the one or more silicone oils of the present disclosure is a non-amino silicone oil such as a dimethicone.

Non-limiting examples of amino-functionalized silicones include bis-hydroxy/methoxy amodimethicones, bis-cetearyl alkoxy) amodimethicone, amodimethicone, bis(C13-15 alkoxy) PG amodimethicones, aminopropyl phenyl trimethicones, aminopropyl dimethicones, bis-amino PEG/PPG-41/3 aminoethyl PG-propyl dimethicones, caprylyl methicones, and a mixture thereof. In some instances, a particularly useful amino-functionalized silicone is bis-hydroxy/methoxy amodimethicone, wherein X is isobutyl and one of the R is OH and the other is $OCH_3$ in the above structure, also known as "Bis-Hydroxy/Methoxy Amodimethicone" and "3-[(2-aminoethyl)amino]-2-methylpropyl Me, di-Me, [(hydroxydimethylsilyl)oxy]- and [(methoxydimethylsilyl)oxy]-terminated." Bis-hydroxy/methoxy amodimethicone is commercially available under the tradename DOWSIL AP-8087 FLUID from The Dow Chemical Company. A non-limiting example of amodimethicone products containing amino silicones having structure (D) re sold by Wacker under the name BELSIL ADM 652, BELSIL ADM 4000 E, or BELSIL ADM LOG 1. A product containing amino silicones having structure (E) is sold by Wacker under the name FLUID WR 1300. Additionally or alternative, the weight-average molecular weight (Mw) of the silicone ranges preferably from 2,000 to 200,000, even more particularly 5,000 to 100,000 and more particularly from 10,000 to 50,000.

The silicone(s) in the hair care compositions of the instant disclosure are included in the form of a silicone emulsion comprising at least one silicone and at least one surfactants, for example, nonionic surfactants, cationic surfactants, amphoteric surfactants, anionic surfactants. The silicone emulsions can be nanoemulsions, microemulsions or macroemulsions. Suitable examples of nonionic surfactants are alkoxylated fatty alcohols or polyethylene glycol ethers of mixtures of C8-C30 fatty alcohols with an average of number of moles of ethylene oxide such as C11-15 Pareth-7, laureth-9, laureth-12, deceth-7, deceth-10, trideceth-6, trideceth-10, trideceth-12, or a mixture thereof. Suitable examples of amphoteric surfactants are cocamidopropyl betaine, coco-betaine, or a mixture thereof. Suitable examples of cationic surfactants are quaternary ammonium compounds such as behentrimonium chloride, cetrimoinium chloride, behentrimonium methosulfate, or a mixture thereof. Suitable examples of anionic surfactants are sulfate-based compounds such as further comprises up to 5 wt. % of a surfactant, for example, sodium (or ammonium) lauryl sulfate, sodium (or ammonium) laureth sulfate, or mixtures thereof.

Thickening Agent(s)

The hair care compositions described herein include one or more thickening agent(s). The amount of thickening agents can vary but is typically from about 0.1 to about 7 wt. %, based on the total weight of the hair care composition. In some instances, the amount of thickening agents present in the hair cosmetic compositions is about 0.1 to about 7 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; about 0.5 to about 7 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; about 1 to about 7 wt. %, about 1 to about 6 wt. %, about 1 to about 5 wt. %, about 1 to about 4 wt. %, about 1 to about 3 wt. %, about 1 to about 2 wt. %, including all ranges and sub-ranges therebetween, based on the total weight of the hair cosmetic composition.

According to preferred embodiments, the thickening agent is an anionic acrylic polymer further comprising at least one monomer performing a strong acid function such as, for example, monomers having a function of the sulfonic acid type or phosphonic acid type, such as 2-acrylamido-2-methylpropane sulfonic acid (AMPS).

According to preferred embodiments, the anionic acrylic polymer may be crosslinked (or branched). Suitable examples of acceptable crosslinking agents include, but are not limited to, methylene bisacrylamide (MBA), ethylene glycol diacrylate, polyethylene glycol dimethacrylate, diacrylamide, cyanomethacrylate, vinyloxyethacrylate or methacrylate, formaldehyde, glyoxal, and compositions of the glycidylether type such as ethyleneglycol diglycidylether, or epoxydes.

Particularly preferred thickening agents are of the taurate copolymer type.

Suitable examples are sodium acrylate/sodium acryloyldimethyl taurate copolymer, acrylamide/sodium acryloyldimethyltaurate copolymer, ammonium polyacryloyldimethyl taurate, ammonium acryloydimethyl taurate/VP copolymer, ammonium polyacryloyldimethyl taurate, ammonium acryloydimethyltaurate/steareth-25 methacrylate crosspolymer, ammonium acryloydimethyltaurate/steareth-8 methacrylate copolymer, sorbitol/sebacic acid copolymer behenate, ethylenediamines/stearyl dimer dilinoleate copolymer, acrylamide/sodium acryloyldimethyltaurate copolymer, and mixtures thereof.

Other suitable examples include cross- or co-polymers of polyacryloyl/taurate or polyacryloyl/dimethyltaurate. Non-limiting examples of such polymers include ammonium acryloyldimethyltaurate/steareth-25 methacrylate crosspolymer, ammonium acryloyldimethyltaurate/steareth-8 methacrylate copolymer, ammonium acryloyldimethyltaurate/beheneth-25 methacrylate crossopolymer, and ammonium acryloyldimethyltaurate/laureth-7 methacrylate copolymer, and mixtures thereof.

A commercially available product containing a thickening agent is sold under the INCI name Sodium Acrylate/Sodium Acryloyldimethyl Taurate Copolymer and Hydrogenated Polydecene and Sorbitan Laurate and Trideceth-6 which is marketed by Arch Personal Care Products, South Plainfield, N.J., USA under the tradename ViscUp®EZ. Other commercially available products include SEPPIC's SEPIPLUS S (hydroxyethyl acrylate sodium acryloyldimethyl taurate copolymer and polyisobutene and PEG-7 trimethyloylpropane coconut ether) and SEPINOV EMT 10 (hydroxyethyl acrylate sodium acryloyldimethyl taurate copolymer).

According to other embodiments of the present invention, the thickening agent is in powder form. Suitable examples of such a thickening agent include SEPINOV EMT 10 discussed above and SEPIMAX Zen (polyacrylate crosspolymer 6).

According to preferred embodiments of the present invention, the thickening agent comprises an acrylamide monomer. Examples are optionally crosslinked and/or neutralized 2-acrylamido-2-methylpropanesulfonic acid polymers and copolymers, for instance poly(2-acrylamido-2-methylpropanesulfonic acid) such as those sold under the tradename HOSTACERIN AMPS (INCI name: ammonium polyacryldimethyltauramide) by the company Clariant, cross-linked anionic copolymers of acrylamide and of AMPS, e.g. in the form of a water-in-oil emulsion, such as those sold under the tradename SEPIGEL 305 (INCI name: Polyacrylamide/C13-14 Isoparaffin/Laureth-7) and under the tradename SIMULGEL 600 (CTFA name: Acrylamide/Sodium acryloyldimethyltaurate copolymer/Isohexadecane/Polysorbate 80) by the company Seppic.

In embodiment, the thickening agent in the compositions of the present disclosure comprise hydroxyethyl acrylate/ sodium acryloyldimethyl taurate copolymer. This thickening agent may be commercially available as a mixture with sorbitan isostearate and polysorbate 60 under the tradename SEPINOV EMT 10 from the company Seppic.

The thickening agent(s) may be chosen from guar gum, biosaccharide gum, cellulose, acacia seneca gum, sclerotium gum, agarose, pechtin, gellan gum, hyaluronic acid. In some cases, the hair cosmetic composition may be free of or substantially free of xanthan gum.

Additionally or alternatively, the one or more thickening agents may include polymeric thickening agents selected from the group consisting of ammonium polyacryloyldimethyl taurate, ammonium acryloyldimethyltaurate/VP copolymer, sodium polyacrylate, acrylates copolymers, polyacrylamide, carbomer, and acrylates/C10-30 alkyl acrylate crosspolymer. Further examples of thickening agents, which may be suitable, can be found in U.S. patent application Ser. No. 16/731,654, which is incorporated herein, in its entirety for all purposes.

Many thickening agents are water-soluble, and increase the viscosity of water or form an aqueous gel when the cosmetic composition of the invention is dispersed/dissolved in water. The aqueous solution may be heated and cooled, or neutralized, for forming the gel, if necessary. The thickening agent may be dispersed/dissolved in an aqueous solvent that is soluble in water, e.g., ethyl alcohol when it is dispersed/dissolved in water.

Particular types of thickening agents that may be mentioned include the following:

One or more thickening agents can optionally be included in the cosmetic compositions of the instant disclosure. Thickening agents may be referred to as "thickeners" or "viscosity modifying agents." Thickening agents are typically included to increase the viscosity of the cosmetic compositions. Nonetheless, in some instances, certain thickening agents provide additional, surprising benefits to the hair cosmetic compositions. Non-limiting examples of thickening agents include polyacrylate crosspolymers or crosslinked polyacrylate polymers, cationic acrylate copolymers, anionic acrylic or carboxylic acid polymers, polyacrylamide polymers, polysaccharides such as cellulose derivatives, gums, polyquaterniums, vinylpyrrolidone homopolymers/copolymers, $C_{8-24}$ hydroxyl substituted aliphatic acid, $C_{8-24}$ conjugated aliphatic acid, sugar fatty esters, polyglyceryl esters, and a mixture thereof. Particular types of thickening agents that may be mentioned include the following:

(i) Carboxylic Acid or Carboxylate Based Homopolymer or Co-Polymer, which can be Linear or Crosslinked:

These polymers contain one or more monomers derived from acrylic acid, substituted acrylic acids, and salts and esters of these acrylic acids (acrylates) and the substituted acrylic acids. Commercially available polymers include those sold under the trade names CARBOPOL, ACRYSOL, POLYGEL, SOKALAN, CARBOPOL ULTREZ, and POLYGEL. Examples of commercially available carboxylic acid polymers include the carbomers, which are homopolymers of acrylic acid cross-linked with allyl ethers of sucrose or pentaerytritol. The carbomers are available as the CARBOPOL 900 series from B.F. Goodrich (e.g., CARBOPOL 954). In addition, other suitable carboxylic acid polymeric agents include ULTREZ 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as CARBOPOL 1342, CARBOPOL 1382, PEMULEN TR-1, and PEMULEN TR-2, from B.F. Goodrich.

Other suitable carboxylic acid or carboxylate polymeric agents include copolymers of acrylic acid and alkyl C5-C10 acrylate, copolymers of acrylic acid and maleic anhydride, and polyacrylate crosspolymer-6. Polyacrylate Crosspolymer-6 is available in the raw material known as SEPIMAX ZEN from Seppic.

Another suitable carboxylic acid or carboxylate polymeric agent includes acrylamidopropyltrimonium chloride/acrylates copolymer, a cationic acrylates copolymer (or a quaternary ammonium compound), available as a raw material known under the tradename of SIMULQUAT HC 305 from Seppic.

In certain embodiments, the carboxylic acid or carboxylate polymer thickening agents useful herein are those selected from carbomers, acrylates/C10-C30 alkyl acrylate crosspolymers, polyacrylate crosspolymer-6, acrylamidopropyltrimonium chloride/acrylates copolymer, and mixtures thereof.

(ii) Celluloses:

Non-limiting examples of celluloses include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. In some instances, the cellulose is selected from water-soluble cellulose derivatives (for example, carboxymethyl cellulose, methyl cellulose, methylhydroxypropyl cellulose, hydroxyethyl cellulose, hydroxypropyl cellulose, cellulose sulfate sodium salt). Furthermore, in some instance, the cellulose is preferably hydroxypropylcellulose (HPC).

Polyvinylpyrrolidone (PVP) and Co-Polymers:

Non-limiting examples include Polyvinylpyrrolidone (PVP), Polyvinylpyrrolidone(PVP)/vinyl acetate copolymer (PVP/VA copolymer), polyvinylpyrrolidone (PVP)/eicosene copolymer, PVP/hexadecene copolymer, etc. Commercially available polyvinylpyrrolidone includes LUVISKOL K30, K85, K90 available from BASF. Commerically available copolymers of vinylpyrrolidone and vinylacetate include LUVISKOL VA37, VA64 available from BASF; copolymers of vinylpyrrolidone, methacrylamide, and vinylimidazole (INCI: VP/Methacrylamide/Vinyl Imidazole Copolymer) is commercially available as LUVISET from BASF. In some instances, PVP and PVP/VA copolymer are preferred.

(iv) Sucrose Esters:

Non-limiting examples include sucrose palmitate, sucrose cocoate, sucrose monooctanoate, sucrose monodecanoate, sucrose mono- or dilaurate, sucrose monomyristate, sucrose mono- or dipalmitate, sucrose mono- and distearate, sucrose mono-, di- or trioleate, sucrose mono- or dilinoleate, sucrose pentaoleate, sucrose hexaoleate, sucrose heptaoleate or sucrose octooleate, and mixed esters, such as sucrose palmitate/stearate, and mixtures thereof.

(v) Polyglyceryl Esters:

Non-limiting polyglycerol esters of fatty acids (polygylceryl esters) include those of the following formula:

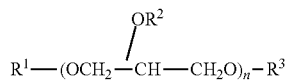

wherein n is from 2 to 20 or from 2 to 10 or from 2 to 5, or is 2, 3, 4, 5, 6, 7, 8, 9, or 10, and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$. Additionally, non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and mixtures thereof.

(vi) Gums:

Non-limiting examples of gums include gum arabic, tragacanth gum, karaya gum, guar gum, gellan gum, tara gum, locust bean gum, tamarind gum, locust bean gum, Seneca gum, sclerotium gum, gellan gum, etc.

Polyol(s)

The hair care composition may, preferably, include one or more polyols. The total amount of polyols in the hair care composition may vary from, e.g., about 0.5 to about 30 wt. %, based on the total weight of the hair care composition. For example, the total amount of polyols may be from about 0.5 to about 30 wt. %, about 0.5 to about 25 wt. %, about 0.5 to 20 wt. %, about 0.5 to about 18 wt. %, about 0.5 to about 16 wt. %, about 0.5 to about 14 wt. %, about 0.5 to about 12 wt. %, about 0.5 to about 10 wt. %, about 0.5 to about 8 wt. %, about 0.5 to about 7 wt. %, about 0.5 to about 6 wt. %, about 0.5 to about 5 wt. %; about 1 to about 30 wt. %, about 1 to about 25 wt. %, about 1 to about 20 wt. %, about 1 to about 18 wt. %, about 1 to about 16 wt. %, about 1 to about 14 wt. %, about 1 to about 12 wt. %, about 1 to about 10 wt. %, about 1 to about 8 wt. %, about 1 to about 7 wt. %, about 1 to about 6 wt. %, about 1 to about 5 wt. %; about 2 to about 30 wt. %, about 2 to about 25 wt. %, about 2 to about 20 wt. %, about 2 to about 18 wt. %, about 2 to about 16 wt. %, about 2 to about 14 wt. %, about 2 to about 12 wt. %, about 2 to about 10 wt. %, about 2 to about 8 wt. %, about 2 to about 7 wt. %, about 2 to about 6 wt. %, about 2 to about 5 wt. %; about 3 to about 30 wt. %, about 3 to about 25 wt. %, about 3 to about 20 wt. %, about 3 to about 18 wt. %, about 3 to about 16 wt. %, about 3 to about 14 wt. %, about 3 to about 12 wt. %, about 3 to about 10 wt. %, about 3 to about 8 wt. %, about 3 to about 7 wt. %, about 3 to about 6 wt. %, about 3 to about 5 wt. %; about 4 to about 30 wt. %, about 4 to about 25 wt. %, about 4 to about 20 wt. %, about 4 to about 18 wt. %, about 4 to about 16 wt. %, about 4 to about 14 wt. %, about 4 to about 12 wt. %, about 4 to about 10 wt. %, about 4 to about 8 wt. % about 4 to about 7 wt. %, about 4 to about 6 wt. %, about 4 to about 5 wt. %; about 5 to about 30 wt. %, about 5 to about 25 wt. %, about 5 to about 20 wt. %, about 5 to about 18 wt. %, about 5 to about 16 wt. %, about 5 to about 14 wt. %, about 5 to about 12 wt. %, about 5 to about 10 wt. %, about 5 to about 8 wt. %, about 5 to about 7 wt. %, about 5 to about 6 wt. %; about 7 to about 30 wt. %, about 7 to about 25 wt. %, about 7 to about 20 wt. %, about 7 to about 18 wt. %, about 7 to about 16 wt. %, about 7 to about 14 wt. %, about 7 to about 12 wt. %, including all ranges and subranges therebetween, based on the total weight of the hair care composition.

The polyols of the hair care composition may comprise or be chosen from polyols having from 2 to 15 carbon atoms and at least two hydroxyl groups. Exemplary polyols that may be used in the hair care composition include and/or may be chosen from alkanediols such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, caprylyl glycol, 1,2-hexanediol, 1,2-pentanediol, and 4-methyl-1,2-pentanediol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; sorbitol; sorbitan; triacetin; and a mixture thereof.

The polyol(s) may be glycols or glycol ethers such as, e.g., monomethyl, monoethyl and monobutyl ethers of ethylene glycol, propylene glycol or ethers thereof such as, e.g., monomethyl ether of propylene glycol, butylene glycol, hexylene glycol, dipropylene glycol as well as alkyl ethers of diethylene glycol, e.g., monoethyl ether or monobutyl ether of diethylene glycol. In one instance, the one or more polyols include or are chosen from ethylene glycol, propylene glycol, butylene glycol, hexylene glycol, pentylene glycol, 1,3-propanediol, diethylene glycol, dipropylene glycol, caprylyl glycol, glycerin, and a mixture thereof. In another instance, the hair care composition includes or is chosen from caprylyl glycol, glycerin, and a mixture thereof.

Cationic Polymer(s)

The hair care compositions may include one or more cationic polymers. The amount of cationic polymers in the hair treatment composition typically ranges from about 0.01 to about 10 wt. % of the total weight of the hair treatment composition. In some instances, the conditioning agents are in an amount ranging from about 0.01 to about 10 wt. %, about 0.01 to about 8 wt. %, about 0.01 to about 6 wt. %, about 0.01 to about 5 wt. %, about 0.01 to about 4 wt. %, about 0.01 to about 3 wt. %, about 0.01 to about 2 wt. %, about 0.01 to about 1 wt. %; about 0.1 to about 10 wt. %, about 0.1 to about 8 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; about 0.25 to about 10 wt. %, about 0.25 to about 8 wt. %, about 0.25 to about 6 wt. %, about 0.25 to about 5 wt. %, about 0.25 to about 4 wt. %, about 0.25 to about 3 wt. %, about 0.25 to about 2 wt. %, about 0.25 to about 1 wt. %; about 0.5 to about 10 wt. %, about 0.5 to about 8 wt. %, about 0.5 to about 6 wt. %, about 0.5 to about 5 wt. %; about 1 to about 10 wt. %, about 1 to about 8 wt. %, about 1 to about 6 wt. %, about 1 to about 5 wt. %; about 2 to about 10 wt. %, about 2 to about 8 wt. %, about 2 to about 6 wt. %, or about 2 to about 5 wt. %, including ranges and sub-ranges therebetween, based on the total weight of the hair care composition.

The cationic polymers can comprise mixtures of monomer units derived from amine- and/or quaternary ammonium-substituted monomer and/or compatible spacer monomers. Suitable cationic polymers include, for example: copolymers of 1-vinyl-2-pyrrolidine and 1-vinyl-3-methyl-imidazolium salt (e.g., chloride salt) (referred to as Polyquaternium-16) such as those commercially available from BASF under the LUVIQUAT tradename (e.g., LUVIQUAT FC 370); copolymers of 1-vinyl-2-pyrrolidine and dimethylaminoethyl methacrylate (referred to as Polyquaternium-11) such as those commercially from Gar Corporation (Wayne, N.J., USA) under the GAFQUAT tradename (e.g., GAFQUAT 755N); and cationic diallyl quaternary ammonium-containing polymer including, for example, dimethyldiallyammonium chloride homopolymer and copolymers of acrylamide and dimethyldiallyammonium chloride (referred to as Polyquaternium-6 and Polyquaternium-7).

Other cationic polymers that may be used include polysaccharide polymers, such as cationic cellulose derivatives and cationic starch derivatives. Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide (referred to as Polyquaternium-10). Another type of cationic cellulose includes the polymeric quaternary ammonium salts of hydroxyethyl cellulose reacted with lauryl dimethyl ammonium-substituted epoxide (referred to as Polyquaternium-24). These materials are available from Amerchol Corp. (Edison, N.J., USA) under the tradename Polymer LM-200. Additionally or alternatively, the cationic conditioning polymers may include or be chosen from cationic guar gum derivatives, such as guar hydroxypropyltrimonium chloride.

The hair treatment composition may include or be chosen from polyquaterniums. For example, the hair treatment composition may include Polyquaternium-1 (ethanol, 2,2', 2"-nitrilotris-, polymer with 1,4-dichloro-2-butene and N,N,N',N'-tetramethyl-2-butene-1,4-diamine), Polyquaternium-2, (poly[bis(2-chloroethyl) ether-alt-1,3-bis[3-(dimethylamino)propyl]urea]), Polyquaternium-4, (hydroxyethyl cellulose dimethyl diallylammonium chloride copolymer; Diallyldimethylammonium chloride-hydroxyethyl cellulose copolymer), Polyquaternium-5 (copolymer of acrylamide and quaternized dimethylammoniumethyl methacrylate), Polyquaternium-6 (poly(diallyldimethylammonium chloride)), Polyquaternium-7 (copolymer of acrylamide and diallyldimethylammonium chloride), Polyquaternium-8 (copolymer of methyl and stearyl dimethylaminoethyl ester of methacrylic acid, quaternized with dimethylsulphate), Polyquaternium-9 (homopolymer of N,N-(dimethylamino)ethyl ester of methacrylic acid, quaternized with bromomethane), Polyquaternium-10 (quaternized hydroxyethyl cellulose), Polyquaternium-11 (copolymer of vinylpyrrolidone and quaternized dimethylaminoethyl methacrylate), Polyquaternium-12 (ethyl methacrylate/abietyl methacrylate/diethylaminoethyl methacrylate copolymer quaternized with dimethyl sulfate), Polyquaternium-13 (ethyl methacrylate/oleyl methacrylate/diethylaminoethyl methacrylate copolymer quaternized with dimethyl sulfate), Polyquaternium-14 (trimethylaminoethylmethacrylate homopolymer), Polyquaternium-15 (acrylamide-dimethylaminoethyl methacrylate methyl chloride copolymer), Polyquaternium-16 (copolymer of vinylpyrrolidone and quaternized vinylimidazole), Polyquaternium-17 (adipic acid, dimethylaminopropylamine and dichloroethylether copolymer), Polyquaternium-18 (azelanic acid, dimethylaminopropylamine and dichloroethylether copolymer), Polyquaternium-19 (copolymer of polyvinyl alcohol and 2,3-epoxypropylamine), Polyquaternium-20 (copolymer of polyvinyl octadecyl ether and 2,3-epoxypropylamine), Polyquaternium-22 (copolymer of acrylic acid and diallyldimethylammonium chloride), Polyquaternium-24 (auaternary ammonium salt of hydroxyethyl cellulose reacted with a lauryl dimethyl ammonium substituted epoxide), Polyquaternium-27 (block copolymer of Polyquaternium-2 and Polyquaternium-17), Polyquaternium-28 (copolymer of vinylpyrrolidone and methacrylamidopropyl trimethylammonium), Polyquaternium-29 (chitosan modified with propylen oxide and quaternized with epichlorhydrin), Polyquaternium-30 (ethanaminium, N-(carboxymethyl)-N,N-dimethyl-2-[(2-methyl-1-oxo-2-propen-1-yl)oxy]-, inner salt, polymer with methyl 2-methyl-2-propenoate), Polyquaternium-31 (N,N-dimethylaminopropyl-N-acrylamidine quaternized with diethylsulfate bound to a block of polyacrylonitrile), Polyquaternium-32 (poly(acrylamide 2-methacryloxyethyltrimethyl ammonium chloride)), Polyquaternium-33 (copolymer of trimethylaminoethylacrylate salt and acrylamide), Polyquaternium-34 (copolymer of 1,3-dibromopropane and N,N-diethyl-N',N'-dimethyl-1,3-propanediamine), Polyquaternium-35 (methosulphate of the copolymer of methacryloyloxyethyltrimethylammonium and of methacryloyloxyethyldimethylacetylammonium), Polyquaternium-36 (copolymer of N,N-dimethylaminoethylmethacrylate and buthylmethacrylate, quaternized with dimethylsulphate), Polyquaternium-37 (poly(2-methacryloxyethyltrimethylammonium chloride)), Polyquaternium-39 (terpolymer of acrylic acid, acrylamide and diallyldimethylammonium Chloride), Polyquaternium-42 (poly[oxyethylene(dimethylimino)ethylene (dimethylimino)ethylene dichloride]), Polyquaternium-43 (copolymer of acrylamide, acrylamidopropyltrimonium chloride, 2-amidopropylacrylamide sulfonate and dimethylaminopropylamine), Polyquaternium-44 (3-Methyl-1-vinylimidazolium methyl sulfate-N-vinylpyrrolidone copolymer), Polyquaternium-45 (copolymer of (N-methyl-N-ethoxyglycine)methacrylate and N,N-dimethylaminoethylmethacrylate, quaternized with dimethyl sulphate), Polyquaternium-46 (terpolymer of vinylcaprolactam, vinylpyrrolidone, and quaternized vinylimidazole), Polyquaternium-47 (terpolymer of acrylic acid, methacrylamidopropyl trimethylammonium chloride, and methyl acrylate), and/or Polyquaternium-67.

In some instances, the hair treatment compositions of the instant disclosure include one or more cationic polymers selected from cationic cellulose derivatives, quaternized hydroxyethyl cellulose (e.g., polyquaternium-10), cationic starch derivatives, cationic guar gum derivatives, copolymers of acrylamide and dimethyldiallyammonium chloride (e.g., polyquaternium-7), polyquaterniums, and a mixture thereof. For example, the cationic polymer(s) may be selected from polyquaterniums, for example, polyquaterniums selected from polyquaternium-4, polyquaternium-5, polyquaternium-6, polyquaternium-7, polyquaternium-10, polyquaternium-22, polyquaternium-37, polyquaternium-39, polyquaternium-47, polyquaternium-53, polyquaternium-67 and a mixture thereof. A combination of two or more polyquaterniums can be useful.

In one instance, the one or more cationic polymers is chosen from polyquaternium 4, polyquaternium 6, polyquaternium 7, polyquaternium 10, polyquaternium 11, polyquaternium 16, polyquaternium 22, polyquaternium 28, polyquaternium 32, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, guar hydroxypropyltrimonium chloride, and a mixture thereof.

Water

The hair care composition may include an amount of water that may be from about 30 to about 95 wt. %, based on the total weight of the hair care composition. In some cases, the hair care composition includes water in amount of about 30 to about 95 wt. %, about 35 to about 95 wt. %, about 40 to about 95 wt. %, about 45 to about 95 wt. %, about 50 to about 95 wt. %, about 55 to about 95 wt. %, about 60 to about 95 wt. %; about 30 to about 90 wt. %, about 35 to about 90 wt. %, about 40 to about 90 wt. %, about 45 to about 90 wt. %, about 50 to about 90 wt. %, about 55 to about 90 wt. %, about 60 to about 90 wt. %; about 30 to about 85 wt. %, about 35 to about 85 wt. %, about 40 to about 85 wt. %, about 45 to about 85 wt. %, about 50 to about 85 wt. %, about 55 to about 85 wt. %, about 60 to about 85 wt. %; about 30 to about 80 wt. %, about 35 to about 80 wt. %, about 40 to about 80 wt. %, about 45 to about 80 wt. %, about 50 to about 80 wt. %, about 55 to about 80 wt. %, about 60 to about 80 wt. %; about 30 to about 75 wt. %, about 35 to about 75 wt. %, about 40 to about 75 wt. %, about 45 to about 75 wt. %, about 50 to about 75 wt. %, about 55 to about 75 wt. %, about 60 to about 75 wt. %; about 30 to about 70 wt. %, about 35 to about 70 wt. %, about 40 to about 70 wt. %, about 45 to about 70 wt. %, about 50 to about 70 wt. %, about 55 to about 70 wt. %, about 60 to about 70 wt. %, including ranges and subranges therebetween, based on the total weight of the hair care composition.

pH Adjuster(s)

The hair care composition may include one or more pH adjusters to increase or decrease the overall pH of the hair care composition. For example, one or more acids may be included to decrease the pH of the hair care composition. Examples of suitable acids for decreasing the pH of the hair care composition include, but are not limited to, citric acid, acetic acid, and the like. The hair care composition may include one or more bases, such as sodium hydroxide, potassium hydroxide and the like, to increase the pH of the hair care composition. Additional or alternative acids and bases that are suitable for adjusting the pH of the hair care composition are readily known to one of ordinary skill in the art.

The amount of the pH adjuster in the hair care composition may be based on the desired pH of the final hair care composition and/or product. For example, the hair care composition may have an amount of pH adjusters such that the pH of the composition is about 3 to about 9, preferably about 3.5 to about 8.

The amount of the pH adjuster in the hair care composition may be based on the desired pH of the final hair care composition and/or product. For example, the total amount of the pH adjuster may range from about 0.05 to about 20 wt. %, based on the total weight of the hair care composition. In some instances, the total amount of pH adjuster is from about 0.05 to about 15 wt. %, about 0.1 to about 10 wt. %, or about 0.12 to about 5 wt. %, including ranges and sub-ranges therebetween, based on the total weight of the hair care composition.

Chelating Agent(s)

The hair care composition may, optionally, include chelating agents. The amount of chelating agent present in the hair care composition may be, e.g., about 0.01 to about 20 wt. %, about 0.01 to about 15 wt. %, about 0.01 to about 10 wt. %, about 0.01 to about 8 wt. %, about 0.01 to about 6 wt. %, about 0.01 to about 5 wt. %, about 0.01 to about 4 wt. %, about 0.01 to about 3 wt. %, about 0.01 to about 2 wt. %, about 0.01 to about 1 wt. %; about 0.1 to about 20 wt. %, about 0.1 to about 15 wt. %, about 0.1 to about 10 wt. %, about 0.1 to about 8 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; about 0.25 to about 20 wt. %, about 0.25 to about 15 wt. %, about 0.25 to about 10 wt. %, about 0.25 to about 8 wt. %, about 0.25 to about 6 wt. %, about 0.25 to about 5 wt. %, about 0.25 to about 4 wt. %, about 0.25 to about 3 wt. %, about 0.25 to about 2 wt. %, about 0.25 to about 1 wt. %; about 0.5 to about 20 wt. %, about 0.5 to about 15 wt. %, about 0.5 to about 10 wt. %, about 0.5 to about 8 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; about 0.75 to about 20 wt. %, about 0.75 to about 15 wt. %, about 0.75 to about 10 wt. %, about 0.75 to about 8 wt. %, about 0.75 to about 6 wt. %, about 0.75 to about 5 wt. %, about 0.75 to about 4 wt. %, about 0.75 to about 3 wt. %, about 0.75 to about 2 wt. %; about 1 to about 20 wt. %, about 1 to about 15 wt. %, about 1 to about 10 wt. %, about 1 to about 8 wt. %, about 1 to about 6 wt. %, about 1 to about 5 wt. %, about 1 to about 4 wt. %, about 1 to about 3 wt. %, or about 1 to about 2 wt. %, including ranges and subranges therebetween, based on the total weight of the hair care composition.

Non-limiting examples of chemical chelating agents include aminotrimethyl phosphonic acid, β-alanine diacetic acid, cyclodextrin, cyclohexanediamine tetracetic acid, diethylenetriamine pentamethylene phosphonic acid, diethanolamine N-acetic acid, ethylene diamine tetracetic acid (EDTA or $YH_4$) and its sodium ($YH_3Na$, $Y_2H_2Na_2$, $YHNa_3$ and $YNa_4$), potassium ($YH_3K$, $Y_2H_3K_3$ and $YK_4$), calcium disodium, and diammonium salts and its salts with triethanolamine (TEA-EDTA), etidronic acid, galactanic acid, hydroxyethyl ethylenediamine tetracetic acid (HEDTA) and its trisodium salt, gluconic acid, glucuronic acid, nitrilotriacetic acid (NTA) and its trisodium salt, pentetic acid, phytic acid, ribonic acid, diammonium citrate, disodium azacycloheptane diphosphonate, disodium pyrophoshate, hydroxypropyl cyclodextrin, methyl cyclodextrin, pentapotassium triphosphate, pentasodium aminotrimethylene phosphonate, pentasodium ethylenediamine tetramethylene phosphonate, pentasodium pentetate, pentasodium triphosphate, potassium citrate, potassium EDTMP, sodium EDTMP, sodium chitosan methylene phosphonate, sodium hexametaphosphate, sodium metaphosphate, potassium polyphosphate, sodium polyphosphate, sodium trimetaphosphate, sodium dihydroxyethylglycinate, potassium gluconate, sodium gluconate, sodium glucopeptate, sodium glycereth-1 polyphosphate, tetrapotassium pyrophosphate, triethanolamine polyphosphate (TEA), tetrasodium pyrophosphate, trisodium phosphate, potassium triphosphonomethylamine oxide, sodium metasilicate, sodium phytate, sodium polydimethylglycinophenolsulfonate, tetrahydroxyethyl ethylene diamine, tetrahydroxypropyl ethylene diamine, tetrapotassium etidronate, tetrasodium etidronate, tetrasodium iminodisuccinate, trisodium ethylenediamine disuccinate, ethanolamine N,N-diacetic acid, disodium acetate, dimercaprol, deferoxamine, Zylox, and/or iron chelating agent disclosed and claimed in the international patent application WO 94/61338, which is incorporated herein in its entirety for all purposes. Examples of biological chelating agents include metallothionein, transferrin, calmodulin, and sodium chitosan methylene phosphonate. In at least one instance, the chelating agent is trisodium ethylenediamine disuccinate.

Preservative(s)

Preservatives may be included in the hair care composition in an amount typically from about 0.01 to about 20 wt. %, about 0.01 to about 18 wt. %, about 0.01 to about 16 wt. %, about 0.01 to about 14 wt. %, about 0.01 to about 12 wt. %, about 0.01 to about 10 wt. %, about 0.01 to about 8 wt. %, about 0.01 to about 7 wt. %, about 0.01 to about 6 wt. %, about 0.01 to about 5 wt. %; about 0.1 to about 20 wt. %, about 0.1 to about 18 wt. %, about 0.1 to about 16 wt. %, about 0.1 to about 14 wt. %, about 0.1 to about 12 wt. %, about 0.1 to about 10 wt. %, about 0.1 to about 8 wt. %, about 0.1 to about 7 wt. %, about 0.1 to about 6 wt. %, about 0.1 to about 5 wt. %; about 1 to about 20 wt. %, about 1 to about 18 wt. %, about 1 to about 16 wt. %, about 1 to about 14 wt. %, about 1 to about 12 wt. %, about 1 to about 10 wt. %, about 1 to about 8 wt. %, about 1 to about 7 wt. %, about 1 to about 6 wt. %, about 1 to about 5 wt. %; about 4 to about 20 wt. %, about 4 to about 18 wt. %, about 4 to about 16 wt. %, about 4 to about 14 wt. %, about 4 to about 12 wt. %, about 4 to about 10 wt. %, about 4 to about 8 wt. %, or about 4 to about 7 wt. %, including all ranges and sub-ranges therebetween, based on the total weight of the hair care composition. Non-limiting examples of preservatives include sodium benzoate, potassium sorbate, phenoxyethanol, salicylic acid, tocopherol, chlorphenesin, BHT, disodium EDTA, pentaerythrityl tetra-di-t-butyl hydroxyhydrocinnamate, and mixtures thereof.

Miscellaneous Ingredient(s)

The hair care compositions may include one or more miscellaneous ingredients, such as colorants, opacifier, absorbents, active ingredients, fragrances, extracts (e.g. natural extracts), fillers (e.g., organic fillers, inorangic fillers, silica, mica, etc.), or the like. The total amount of miscellaneous ingredients is typically about 15 wt. % or less, based on the total weight of the hair care compositions. For example, the hair care composition may include miscellaneous ingredients in an amount of about 12.5 wt. % or less, about 10 wt. % or less, about 8 wt. % or less, about 6 wt. % or less, about 5 wt. % or less, about 4 wt. % or less, about 3 wt. % or less, about 2 wt. % or less, or about 1 wt. % or less, based on the total weight of the hair care composition. In some instances, the amount of miscellaneous ingredients present in the hair care composition is about 0.01 to about 15 wt. %, about 0.01 to about 12.5 wt. %, about 0.01 to about 10 wt. %, about 0.01 to about 8 wt. %, about 0.01 to about 6 wt. %, about 0.01 to about 5 wt. %, about 0.01 to about 4 wt. %, about 0.01 to about 3 wt. %, about 0.01 to about 2 wt. %, about 0.01 to about 1 wt. %; about 0.1 to about 15 wt. %, about 0.1 to about 12.5 wt. %, about 0.1 to about 10 wt. %, about 0.1 to about 8 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; about 0.5 to about 15 wt. %, about 0.5 to about 12.5 wt. %, about 0.5 to about 10 wt. %, about 0.5 to about 8 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; about 1 to about 15 wt. %, about 1 to about 12.5 wt. %, about 1 to about 10 wt. %, about 1 to about 8 wt. %, about 1 to about 6 wt. %, about 1 to about 5 wt. %, about 1 to about 4 wt. %, about 1 to about 3 wt. %, about 1 to about 2 wt. %; about 2 to about 15 wt. %, about 2 to about 12.5 wt. %, about 2 to about 10 wt. %, about 2 to about 8 wt. %, about 2 to about 6 wt. %, about 2 to about 5 wt. %, about 2 to about 4 wt. %; about 4 to about 15 wt. %, about 4 to about 12.5 wt. %, about 4 to about 10 wt. %, about 4 to about 8 wt. %, about 4 to about 6 wt. %; about 6 to about 15 wt. %, about 6 to about 12.5 wt. %, about 6 to about 10 wt. %, about 6 to about 8 wt. %; about 8 to about 15 wt. %, about 8 to about 12.5 wt. %, about 8 to about 10 wt. %; about 10 to about 15 wt. %, about 10 to about 12.5 wt. %; or about 12 to about 15 wt. %, including any ranges and subranges therebetween, based on the total weight of the hair care composition.

Embodiments of the Disclosure

In certain embodiments of the disclosure, provided is a hair care composition comprising:
  one or more nonionic surfactants comprising one or more alkylpolyglucosides, preferably in an amount of about 1 to about 15 wt. %, more preferably in an amount of about 2 to about 13 wt. %, wherein the one or more one or more alkylpolyglucoside comprises $C_{12-20}$ alkyl glucoside and, optionally, the one or more nonionic surfactants further comprises PEG-40 hydrogenated castor oil;
  one or more fatty alcohols, preferably in an amount of about 0.5 to about 10 wt. %, more preferably in an amount of about 1 to about 8 wt. %, wherein the one or more fatty alcohols may comprise $C_{14-22}$ alcohols and/or octyldodecanol;
  one or more fatty esters, preferably in an amount of about 1 to about 20 wt. %, more preferably in an amount of about 3 to about 16 wt. %, the one or more fatty esters comprising caprylic/capric triglyceride and, optionally, isopropyl myristate, glyceryl stearate, sorbitan isostearate, or a mixture thereof;
  about 0.5 to about 30 wt. %, preferably about 0.5 to about 20 wt. %, more preferably about 2 to about 20 wt. %, of a fatty compound other than fatty alcohol and fatty ester, such as isododecane, hydrogenated vegetable oil, butyrospermum parkii (shea) butter, euphorbia cerifera (candelilla) wax, beeswax, or a mixture thereof;
  one or more silicones, preferably in an amount of about 0.5 to about 10 wt. %, more preferably in an amount of about 0.5 to about 6 wt. %, wherein the one or more silicones comprises polysilicone-11 and, optionally, dimethicone;
  one or more thickening agents, preferably in an amount of about about 0.1 to about 7 wt. %, more preferably in an amount about 0.1 to about 5 wt. %, wherein the thickening agents preferably comprises hydroxyethyl acrylate/sodium acryloyldimethyl taurate copolymer; and
  water, preferably in an amount of about 30 to about 95 wt. %, more preferably in an amount of about 45 to about 80 wt. %, wherein the hair care composition is an emulsion, and all weight percentages are based on the total weight of the hair care composition.

In further embodiments of the disclosure, provided is a hair care composition comprising:
  about 2 to about 15 wt. %, preferably about 2 to about 13 wt. %, more preferably about 2 to about 10 wt. %, of one or more nonionic surfactants comprising alkylpolyglucosides, wherein the one or more nonionic surfactants comprises $C_{12-20}$ alkyl glucoside and, optionally, PEG-40 hydrogenated castor oil;
  about 0.5 to about 10 wt. %, more preferably about 1 to about 8 wt. %, more preferably about 1 to about 5 wt. %, of one or more fatty alcohols, wherein the one or more fatty alcohols may comprise $C_{14-22}$ alcohols and/or octyldodecanol;
  about 1 to about 20 wt. %, preferably about 3 to about 20 wt. %, more preferably about 3 to about 16 wt. %, of one or more fatty esters, wherein the one or more fatty esters comprises caprylic/capric triglyceride and, optionally, isopropyl myristate, glyceryl stearate, sorbitan isostearate, or a mixture thereof;
  about 0.5 to about 30 wt. %, preferably about 0.5 to about 20 wt. %, more preferably about 2 to about 20 wt. %, of a fatty compound other than fatty alcohol and fatty ester, such as isododecane, hydrogenated vegetable oil, butyrospermum parkii (shea) butter, euphorbia cerifera (candelilla) wax, beeswax, or a mixture thereof;
  about 0.5 to about 10 wt. %, preferably about 0.5 to about 8 wt. %, more preferably about 0.5 to about 6 wt. %, of one or more silicones, wherein the one or more silicones comprises polysilicone-11 and, optionally, dimethicone;
  about 0.1 to about 10 wt. %, preferably about 0.1 to about 7 wt. %, more preferably about 0.1 to about 5 wt. %, of one or more thickening agent, wherein the thickening agents preferably comprises hydroxyethyl acrylate/sodium acryloyldimethyl taurate copolymer;
  water, preferably in an amount of about 30 to about 95 wt. %, more preferably in an amount of about 45 to about 80 wt. %;
  optionally, about 0.5 to about 30 wt. %, preferably about 0.5 to 20 wt. %, more preferably about 2 to about 20 wt. %, of a polyol, such as those chosen from ethylene glycol, propylene glycol, butylene glycol, hexylene glycol, pentylene glycol, 1,3-propanediol, diethylene glycol, dipropylene glycol, caprylyl glycol, glycerin, and a mixture thereof;
  optionally, about 0.01 to about 10 wt. %, preferably about 0.1 to about 8 wt. %, more preferably about 0.1 to about 6 wt. %, of a cationic polymer chosen from polyquaternium-4, polyquaternium-6, polyquaternium-7, polyquaternium-10, polyquaternium-11, polyquaternium-16, polyquaternium-22, polyquaternium-28, polyquaternium-32, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, guar hydroxypropyltrimonium chloride, and a mixture thereof,
  wherein all weight percentages are based on the total weight of the hair care composition.

In further embodiments of the disclosure, a method is provided for improving hair comprising:
  (I) applying a hair care composition to hair, the hair care composition comprising:
    one or more nonionic surfactants comprising alkylpolyglucosides, preferably in an amount of about 1 to about 15 wt. %, more preferably in an amount of about 2 to about 13 wt. %, wherein the one or more nonionic surfactants may comprise $C_{12-20}$ alkyl glucoside and/or PEG-40 hydrogenated castor oil, one or more fatty alcohols, preferably in an amount of about 0.5 to about 10 wt. %, more preferably in an amount of about 1 to about 8 wt. %, wherein the one or more fatty alcohols may comprise $C_{14-22}$ alcohols and/or octyldodecanol, one or more fatty esters, preferably in an amount of about 1 to about 20 wt. %, more preferably in an amount of about 3 to about 16 wt. %, the one or more fatty esters comprising caprylic/capric triglyceride and, optionally, isopropyl myristate, glyceryl stearate, sorbitan isostearate, or a mixture thereof, about 0.5 to about 30 wt. %, preferably about 0.5 to about 20 wt. %, more preferably about 2 to about 20 wt. %, of a fatty compound other than fatty alcohol and fatty ester, such as isododecane, hydrogenated vegetable oil, butyrospermum parkii (shea) butter, euphorbia cerifera (candelilla) wax, beeswax, or a mixture thereof, one or more silicones, preferably in an amount of about 0.5 to about 10 wt. %, more preferably in an amount of about 0.5 to about 6 wt. %, wherein the one or more silicones comprises polysilicone-11 and, optionally, dimethicone, one or more thickening agents, preferably in an amount of about 0.1 to about 7 wt. %, more preferably in an amount about 0.1 to about 5 wt. %, wherein the thickening agents preferably comprises hydroxyethyl acrylate/sodium acryloyldimethyl taurate copolymer, and water, preferably in an amount of about 30 to about 95 wt. %, more preferably in an amount of about 45 to about 80 wt. %, wherein the hair care composition is an emulsion, and all weight percentages are based on the total weight of the hair care composition;

(II) optionally, rinsing the hair care compositions from the hair.

The terms "comprising," "having," and "including" are used in their open, non-limiting sense. The terms "a" and "the" are understood to encompass the plural as well as the singular. The compositions and methods of the present disclosure can comprise, consist of, or consist essentially of the essential elements and limitations of the disclosure described herein, as well as any additional or optional ingredients, components, or limitations described herein or otherwise useful.

All percentages, parts and ratios herein are based upon the total weight of the compositions of the present disclosure, unless otherwise indicated. All ranges and values disclosed herein are inclusive and combinable. The expression "inclusive" for a range of concentrations means that the limits of the range are included in the defined interval. For examples, any value or point described herein that falls within a range described herein can serve as a minimum or maximum value to derive a sub-range, etc. Furthermore, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

Other than in the operating examples, or where otherwise indicated, all numbers expressing quantities of ingredients and/or reaction conditions are to be understood as being modified in all instances by the term "about," meaning within +/−5% of the indicated number.

As used herein, the expression "at least one" is interchangeable with the expression "one or more" and thus includes individual components as well as mixtures/combinations.

The term "substantially free" or "essentially free" as used herein means that there is less than about 5% by weight of a specific material added to a composition, based on the total weight of the compositions. Nonetheless, the compositions may include less than about 2 wt. %, less than about 1 wt. %, less than about 0.5 wt. %, less than about 0.1 wt. %, less than 0.01 wt. %, or none of the specified material.

The term "active material" as used herein with respect to the percent amount of an ingredient or raw material, refers to 100% activity of the ingredient or raw material.

Throughout the disclosure, the term "a mixture thereof" may be used following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included. The salts referred to throughout the disclosure may include salts having a counter-ion such as an alkali metal, alkaline earth metal, or ammonium counter-ion. This list of counter-ions, however, is non-limiting.

"Volatile", as used herein, means having a flash point of less than about 100° C. "Non-volatile", as used herein, means having a flash point of greater than about 100° C.

The term "polymers," as defined herein, include homopolymers and copolymers formed from at least two different types of monomers.

The term "INCI" is an abbreviation of International Nomenclature of Cosmetic Ingredients, which is a system of names provided by the International Nomenclature Committee of the Personal Care Products Council to describe personal care ingredients.

All components and elements positively set forth in this disclosure can be negatively excluded from the claims. In other words, the compositions (nanoemulsions) of the instant disclosure can be free or essentially free of all components and elements positively recited throughout the instant disclosure.

Some of the various categories of components identified may overlap. In such cases where overlap may exist and the composition includes both components (or the composition includes more than two components that overlap), an overlapping compound does not represent more than one component. For example, a fatty acid may be characterized as both a nonionic surfactant and a fatty compound. If a particular composition includes both a nonionic surfactant and a fatty compound, a single fatty acid will serve as only the nonionic surfactant or as only the fatty compound (the single fatty acid does not serve as both the nonionic surfactant and the fatty compound). However, the fatty compounds (such as a fatty alcohol) may or may not be an oil depending on the particular fatty alcohol.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

EXAMPLES

Implementation of the present disclosure is provided by way of the following examples. The following examples serve to elucidate aspects of the technology without being limiting in nature.

Example 1

Two non-limiting, example compositions (Ex. A and B) were prepared in accordance with aspects of the disclosure. A comparative composition (Comp. 1) was also prepared according to the formula provided below. The formulations for Example Compositions A and B and Comparative Composition 1 are shown in Table 1, below.

behentrimonium chloride, and Comparative Composition 4 included 1 gram of dicetyldimonium chloride instead of the $C_{12-20}$ alkyl glucoside and $C_{14-22}$ alcohols used in Example Composition A. The processing steps for producing Comparative Compositions 2-4 were the same as the processing steps used for producing Example Composition A.

Comparative Compositions 2-4 and Example Compositions A and B were then evaluated to assess the stability of their respective emulsion. Specifically, two samples of Comparative Compositions 2-4 and Example Compositions A and B were maintained at certain environmental conditions for 8 weeks and visually assessed at various times to determine the stability of the respective emulsion. The first sample for each of the compositions was maintained at room temperature and the second sample for each of the compositions was maintained at a temperature of 45° C.

Comparative Composition 2 exhibited an unstable emulsion, with the sample maintained at a temperature of 45° C. exhibiting the hydrophobic phase separating from the hydrophilic phase. The samples for Comparative Composition 3 exhibited an unstable emulsion at room temperature and at a temperature of 45° C. Comparative Composition 4 did not form an emulsion. Example Compositions A and B each exhibited an emulsion that was stable at room temperature and at elevated temperatures. It was surprisingly that the Example Compositions A and B exhibited and maintained a

TABLE 1

| | | US INCI Name | Ex. A | Ex. B | Comp. 1 |
|---|---|---|---|---|---|
| (a) | Nonionic Surfactant | POLYSORBATE 60, and PEG-40 HYDROGENATED CASTOR OIL | 5.1 | 5.1 | 5.1 |
| | | C12-20 ALKYL GLUCOSIDE | 0.2 | 0.2 | 0.2 |
| (b) | Fatty Alcohol | OCTYLDODECANOL | 1 | 1 | 1 |
| | | C14-22 ALCOHOLS | 0.8 | 0.8 | 0.8 |
| (c) | Fatty Ester | ISOPROPYL MYRISTATE, GLYCERYL STEARATE, and SORBITAN ISOSTEARATE | 7.3 | 7.2 | 7.3 |
| | | CAPRYLIC/CAPRIC TRIGLYCERIDE | 0.1 | 0.1 | |
| (d) | Fatty compound other than fatty alcohol and fatty ester | ISODODECANE and HYDROGENATED VEGETABLE OIL | 4.5 | 4 | 4.5 |
| | Wax | BUTYROSPERMUM PARKII (SHEA) BUTTER, EUPHORBIA CERIFERA (CANDELILLA) WAX, and BEESWAX | 2.8 | 1.9 | 2.8 |
| (e) | Silicone | DIMETHICONE | 1.6 | 1.6 | 1.6 |
| | | POLYSILICONE-11 | <0.1 | <0.1 | <0.1 |
| (f) | Acrylic thickening agent | HYDROXYETHYL ACRYLATE/SODIUM ACRYLOYLDIMETHYL TAURATE COPOLYMER | 0.89 | 0.89 | 0.89 |
| (h) | Polyol | GLYCERIN | 10 | 10 | 10 |
| (i) | Cationic polymer | POLYQUATERNIUM-10 | 0.1 | 0.1 | 0.1 |
| | Preservatives | ETHYLHEXYLGLYCERIN, TOCOPHEROL, PHENOXYETHANOL, and CITRIC ACID | ~0.9 | ~0.9 | ~0.9 |
| | Fragrance | FRAGRANCE | <1 | <1 | <1 |
| (g) | Water | WATER | 64.31 | 65.81 | 64.41 |

Example 2

Three comparative compositions (Comparative Compositions 2-4) were prepared to have the same formulation as Example Composition A, except that Comparative Compositions 2-4 had a cationic surfactant instead of the $C_{12-20}$ alkyl glucoside and $C_{14-22}$ alcohols. In particular, Comparative Composition 2 included 1 gram of cetrimonium chloride, Comparative Composition 3 included 1 gram of stable emulsion at room temperature and elevated temperatures as Example Compositions A and B comprised large amounts of oils and silicone compounds.

Example 3

Four comparative compositions (Comparative Compositions 5-8) were prepared to have the same formulation as Example Composition A, except that Comparative Compositions 5-8 had the isopropyl myristate replaced with olive oil, sunflower oil, linseed oil, or alkane esters. Specifically, Comparative Composition 5 included 7 grams of olive oil, Comparative Composition 6 included 7 grams of sunflower oil, Comparative Composition 7 included 7 grams of linseed oil, and Comparative Composition 8 included 7 grams of alkane esters. Additionally, Comparative Compositions 5-8 were produced according to the same processing steps used to produce Example Composition A.

Comparative Compositions 5-8 and Example Compositions A and B were then evaluated to assess their respective conditioning properties. In particular, a sample of Comparative Compositions 5-8 and Example Compositions A and B were separately applied to respective hair swatches in an amount of 2 gram (g) of composition per 10 g of hair. The hair swatches were then combined to ensure a uniform application of the sample onto the hair swatch. The hair swatches were subsequently rinsed. After drying, the hair swatches were evaluated to asses the conditioning properties of the Comparative Compositions 5-8 and Example Compositions A and B.

Comparative Composition 5 provided a very heavy feel to the hair and was unsuitable for leave-in products. Comparative Compositions 6 and 7 resulted in the hair feeling greasy. Comparative Composition 8 did not provide a sufficient coating or a conditioning feel. Example Compositions A and B did not weigh down the hair and provided significant conditioning properties.

Example 4

Four comparative compositions (Comparative Compositions 9-12) were prepared to have the same formulation as Example Composition A, except that Comparative Compositions 9-12 had the octyldodecanol replaced with cetearyl alcohol, glyceryl stearate, cetearyl alcohol in conjuction with cetearyl glucoside, and tribehenin. Specifically, Comparative Composition 9 included 1 grams of cetearyl alcohol, Comparative Composition 10 included 1 grams of glyceryl stearate, Comparative Composition 11 included 0.5 grams of cetearyl alcohol and 0.5 grams of cetearyl glucoside, and Comparative Composition 12 included 1 grams of tribehenin. Additionally, the processing steps for producing Comparative Compositions 9-12 were the same as the processing steps used for producing Example Composition A.

Comparative Compositions 9-12 and Example Compositions A and B were then evaluated to assess the stability of their respective emulsion. Specifically, samples of Comparative Compositions 2-4 and Example Compositions A and B were maintained at room temperature for 8 weeks and visually assessed at various times to determine the stability of the respective emulsion. Comparative Composition 9 did not form a stable emulsion. Comparative Composition 10 was unable to contain the large amounts of oil in the formed emulsion and, thus, the hydrophilic phase separated from the emulsion. Comparative Compositions 11 and 12 also did not form a stable emulsion.

Example 5

Seven comparative compositions (Comparative Compositions 13-19) were prepared to have the same formulation as Example Composition A, except that Comparative Compositions 13-19 had the dimethicone and polysilicone-11 replaced with different dimethicones, dimethiconol, and dimethicone PEG-10/15 cross polymer. Specifically, Comparative Composition 13 included 1.6 g of dimethicone having a viscosity of 350 centistokes (CST). Comparative Composition 14 included 1.6 g of dimethicone having a viscosity of 300,000 CST. Comparative Composition 15 included 1.6 g of dimethicone having a viscosity of 5 CST. Comparative Composition 16 included 1.6 g of a combination of dimethicone and dimethiconol, the combination having a viscosity of 300,000 CST. Comparative Composition 17 included 1.6 g of a combination of dimethicone and dimethicone PEG-10/15 crosspolymer, the combination having a viscosity of 500,000 CST. Comparative Composition 18 included 1.6 g of a dimethicone having a viscosity of 6,900 CST. Comparative Composition 19 included 1.6 g of dimethiconol having a viscosity of 1,500 CST. Additionally, the processing steps for producing Comparative Compositions 13-19 were the same as the processing steps used for producing Example Composition A.

Comparative Compositions 13-19 and Example Compositions A and B were then evaluated to assess the stability and coating properties of their respective compositions. In particular, a sample of Comparative Compositions 13-19 and Example Compositions A and B were separately applied to respective hair swatches in an amount of 2 gram (g) of composition per 10 g of hair. The hair swatches were then combined to ensure a uniform application of the sample onto the hair swatch. The hair swatches were subsequently rinsed. After drying, the hair swatches were evaluated to assess the conditioning properties of the Comparative Compositions 13-19 and Example Compositions A and B.

Comparative Composition 13 provided a light coating on hair, which did not endure after the hair was shampooed. Comparative Composition 14 provided a heavy coating that weighed down the hair. Although Comparative Composition 15 provided a good coating, the coating did not ensure after the hair was shampoo. Comparative Composition 16 provided a slightly heavy coating that was undesirable. Comparative Composition 17 did not form an emulsion. Comparative Composition 18 provided a slightly heavy coating that was undesirable. Comparative Composition 19 provided an undesirably light coating.

Example 6

It is believed that certain exemplary compositions presented in Example 1 produce emulsions with an aqueous phase and an oil phase. Table 2, provided below, shows the combination of certain ingredients in an aqueous phase or in an oil phase before formation of the emulsion as well as the ingredients added after formation of the emulsion.

TABLE 2

| Phase:<br>A = aqueous<br>B = oil<br>E = After<br>formation<br>of Emulsion | US INCI compound name |
|---|---|
| A | C14-22 ALCOHOLS |
| A | C12-20 ALKYL GLUCOSIDE |
| A | POLYQUATERNIUM-10 |
| A | GLYCERIN |
| A | POLYQUATERNIUM-10 |
| A | WATER |
| B | HYDROXYETHYL ACRYLATE/SODIUM ACRYLOYLDIMETHYL TAURATE COPOLYMER |
| B | PEG-40 HYDROGENATED CASTOR OIL |

TABLE 2-continued

| Phase:<br>A = aqueous<br>B = oil<br>E = After formation of Emulsion | US INCI compound name |
|---|---|
| B | HYDROGENATED VEGETABLE OIL |
| B | *EUPHORBIA* CERIFERA (CANDELILLA) WAX |
| B | BEESWAX |
| B | GLYCERYL STEARATE |
| B | ISOPROPYL MYRISTATE |
| B | CAPRYLIC/CAPRIC TRIGLYCERIDE |
| E | OCTYLDODECANOL |
| E | DIMETHICONE |
| E | POLYSILICONE-11 |
| E | PHENOXYETHANOL |
| E | ETHYLHEXYLGLYCERIN |
| E | FRAGRANCE |

The invention claimed is:

1. A hair care composition comprising:
   (a) about 3 to about 9 wt. % of one or more nonionic surfactants, wherein at least one of the one or more nonionic surfactants is a $C_{12-20}$ alkyl glucoside in an amount from about 0.1 to about 3 wt. %;
   (b) about 1 to about 4 wt. % of octyldodecanol and $C_{14-22}$ alcohols, wherein the $C_{14-22}$ alcohols is in an amount from about 0.5 to about 3 wt. %;
   (c) about 5 to about 10 wt. % of isopropyl myristate;
   (d) about 2 to about 10 wt. % of one or more fatty compounds other than (b) and (c);
   (e) about 1 to about 5 wt. % of one or more silicones, wherein at least one of the one or more silicones is polysilicone-11;
   (f) about 0.5 to about 4 wt. % of hydroxyethyl acrylate/sodium acryloyldimethyl taurate copolymer;
   (g) about 40 wt. % or more of water; and
   (h) about 3 to about 20 wt. % of one or more polyols,
      wherein the hair care composition is an emulsion, the hair care composition is visually stable for 8 weeks at a temperature of 45° C., and all weight percentages are based on a total weight of the hair care composition.

2. The hair care composition of claim 1, wherein the one or more silicones further comprises dimethicone, dimethiconol, decamethylcyclopentasiloxane, cyclomethicone, or mixtures thereof.

3. The hair care composition of claim 1, wherein the one or more polyols are chosen from ethylene glycol, propylene glycol, butylene glycol, hexylene glycol, pentylene glycol, diethylene glycol, dipropylene glycol, 1,3 propanediol, glycerin, polyethylene glycols, or mixtures thereof.

4. The hair care composition of claim 1, wherein the one or more fatty compounds other than (b) and (c) comprises one or more waxes, in an amount from about 0.1 to about 10 wt. %.

5. The hair care composition of claim 4, wherein the one or more waxes are chosen from illipe butter, beeswax, butyrospermum parkii butter, euphorbia cerifera wax, carnauba, lanolin, lanolin derivatives, candelilla, cocoa butter, sugar cane wax, montan wax, whale wax, bayberry wax, acacia decurrents flower wax, vegetable waxes, or mixtures thereof.

6. The hair care composition of claim 1 further comprising:
   (i) about 0.01 to about 10 wt. % of one or more cationic polymers.

7. The hair care composition of claim 6, wherein the one or more cationic polymers are chosen from polyquaternium-4, polyquaternium-6, polyquaternium-7, polyquaternium-10, polyquaternium-11, polyquaternium-16, polyquaternium-22, polyquaternium-28, polyquaternium-32, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, guar hydroxypropyltrimonium chloride, or mixtures thereof.

8. The hair care composition of claim 1, wherein a weight ratio of the $C_{12-20}$ alkyl glucoside and the $C_{14-22}$ alcohols to the hydroxyethyl acrylate/sodium acryloyldimethyl taurate copolymer is from about 0.5:1 to about 1:0.5.

9. A method for conditioning hair, the method comprising applying the hair care composition of claim 1 to the hair, and optionally rinsing the composition from the hair.

10. A hair care composition comprising:
   (a) about 3 to about 9 wt. % of one or more nonionic surfactants, wherein one of the one or more nonionic surfactants is an $C_{12-20}$ alkyl glucoside in an amount from about 0.1 to about 3 wt. %;
   (b) about 1 to about 4 wt. % of octyldodecanol and $C_{14-22}$ alcohols, wherein the $C_{14-22}$ alcohols are in an amount from about 0.5 to about 3 wt. %;
   (c) about 5 to about 10 wt. % of two or more fatty esters, wherein one of the two or more fatty esters is caprylic/capric triglyceride in an amount from 0.05 to about 4 wt. % and one of the two or more fatty esters is isopropyl myristate;
   (d) about 2 to about 10 wt. % of one or more fatty compounds other than (b) and (c);
   (e) about 1 to about 5 wt. % of two or more silicones, wherein one of the two or more silicones is polysilicone-11 and one of the two or more silicones is dimethicone;
   (f) about 0.5 to about 4 wt. % of hydroxyethyl acrylate/sodium acryloyldimethyl taurate copolymer;
   (g) about 40 wt. % or more of water; and
   (h) about 3 to about 20 wt. % of one or more polyols chosen from ethylene glycol, propylene glycol, butylene glycol, hexylene glycol, pentylene glycol, diethylene glycol, dipropylene glycol, 1,3 propanediol, glycerin, polyethylene glycols, or mixtures thereof,
      wherein the hair care composition is an emulsion,
      a weight ratio of the $C_{12-20}$ alkyl glucoside and the $C_{14-22}$ alcohols to the hydroxyethyl acrylate/sodium acryloyldimethyl taurate copolymer is from about 0.5:1 to about 1:0.5, and all weight percentages are based on a total weight of the hair care composition.

11. The hair care composition of claim 10, wherein the one or more fatty compounds other than (b) and (c) comprises one or more waxes, in an amount from about 0.5 to about 6 wt.

12. The hair care composition of claim 7, wherein the one or more waxes are chosen from illipe butter, beeswax, butyrospermum parkii butter, euphorbia cerifera wax, carnauba, lanolin, lanolin derivatives, candelilla, cocoa butter, sugar cane wax, montan wax, whale wax, bayberry wax, acacia decurrents flower wax, vegetable waxes, or mixtures thereof.

13. The hair care composition of claim 10 further comprising:
   (i) one or more cationic polymers chosen from polyquaternium-4, polyquaternium-6, polyquaternium-7, polyquaternium-10, polyquaternium-11, polyquaternium-16, polyquaternium-22, polyquaternium-28, polyquaternium-32, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, guar hydroxypropyltrimonium chloride, or mixtures thereof.

14. The hair care composition of claim 10, wherein the composition is visually stable for 8 weeks at a temperature of 45° C.

15. A method for conditioning hair, the method comprising applying the hair care composition of claim 10 to the hair, and optionally rinsing the composition from the hair.

16. The hair care composition of claim 10, wherein the one or more fatty compounds other than (b) and (c) comprises one or more waxes, in an amount from about 0.1 to about 10 wt. %.

17. The hair care composition of claim 10 further comprising:
   (i) about 0.01 to about 10 wt. % of one or more cationic polymers.

18. The hair care composition of claim 17, wherein the one or more cationic polymers are chosen from polyquaternium-4, polyquaternium-6, polyquaternium-7, polyquaternium-10, polyquaternium-11, polyquaternium-16, polyquaternium-22, polyquaternium-28, polyquaternium-32, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, guar hydroxypropyltrimonium chloride, or mixtures thereof.

* * * * *